United States Patent
Nagoh et al.

(10) Patent No.: US 7,169,941 B2
(45) Date of Patent: Jan. 30, 2007

(54) PHOTOCHROMIC COMPOSITION

(75) Inventors: Hironobu Nagoh, Shunan (JP); Junji Momoda, Shunan (JP)

(73) Assignee: Tokuyama Corporation, Yamaguchi-ken (JP)

( * ) Notice: Subject to any disclaimer, the term of this patent is extended or adjusted under 35 U.S.C. 154(b) by 352 days.

(21) Appl. No.: 10/484,349

(22) PCT Filed: May 22, 2002

(86) PCT No.: PCT/JP02/04947

§ 371 (c)(1),
(2), (4) Date: Jan. 21, 2004

(87) PCT Pub. No.: WO03/097765

PCT Pub. Date: Nov. 27, 2003

(65) Prior Publication Data

US 2004/0173782 A1    Sep. 9, 2004

(51) Int. Cl.
*C07D 311/78* (2006.01)

(52) U.S. Cl. .................. 549/381; 252/586; 526/209; 526/319; 549/336

(58) Field of Classification Search ................ 252/586; 526/209, 319; 549/336, 381
See application file for complete search history.

(56) References Cited

U.S. PATENT DOCUMENTS 6,719,925 B1 * 4/2004 Breyne et al. .............. 252/586

FOREIGN PATENT DOCUMENTS

| JP | 2001-11066 A | 1/2001 |
| JP | 2001-114775 A | 4/2001 |
| JP | 2002-161269 A | 6/2002 |
| WO | WO 96/14596 A1 | 5/1996 |
| WO | WO 97/4899 A1 | 12/1997 |
| WO | WO 98/45281 A1 | 10/1998 |

* cited by examiner

*Primary Examiner*—Robert D. Harlan
(74) *Attorney, Agent, or Firm*—Birch, Stewart, Kolasch & Birch, LLP

(57) ABSTRACT

A photochromic composition and a coating composition comprising a molecular compound of a chromene compound and an aromatic compound. The photochromic composition provides a photochromic optical material as a cured product and the coating composition is applied to a lens substrate and cured to provide a photochromic optical material. The above molecular compound is also provided.

15 Claims, 3 Drawing Sheets

F I G. 1
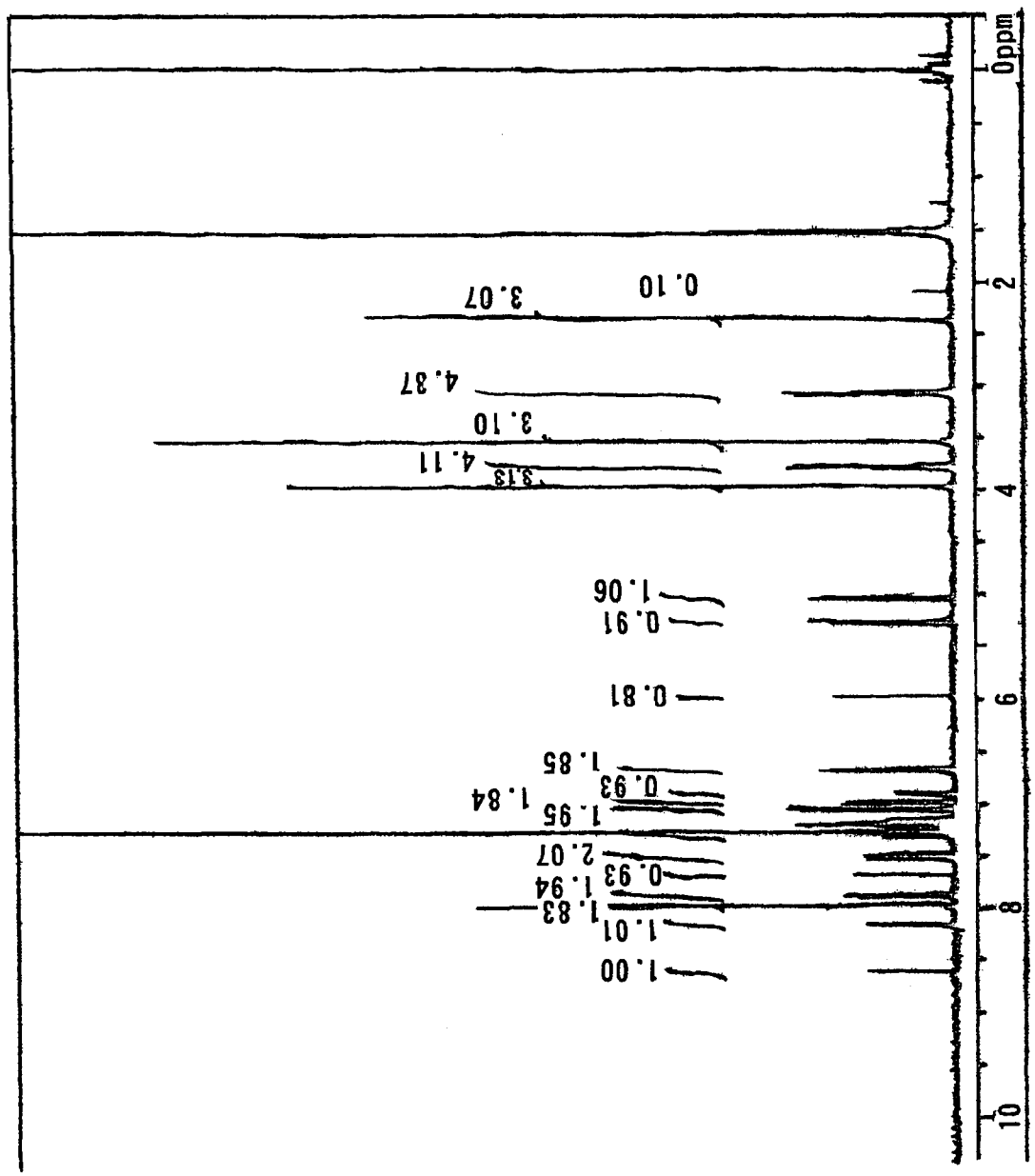

F I G. 2
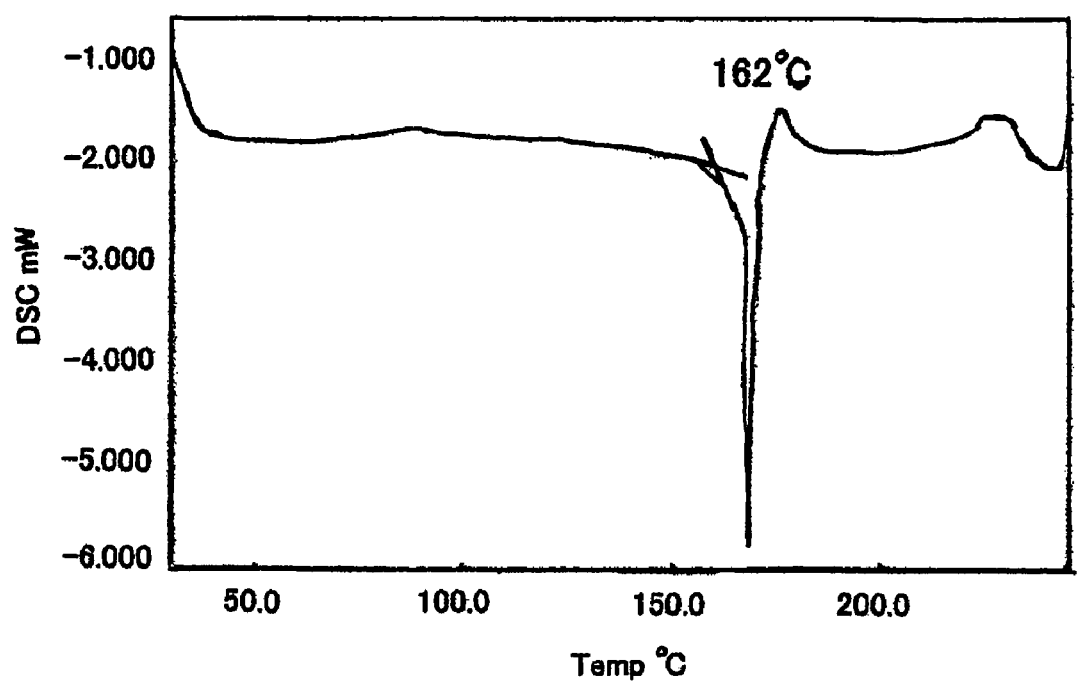

F I G. 3
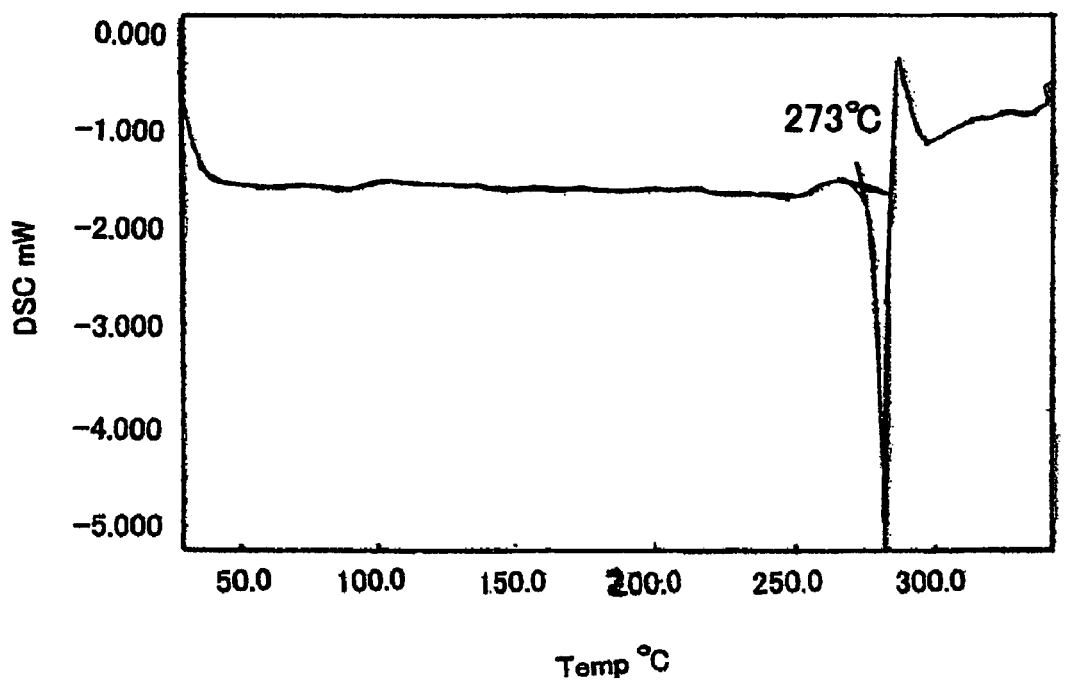

PHOTOCHROMIC COMPOSITION

FIELD OF THE INVENTION

The present invention relates to a photochromic composition which can contain a chromene compound having excellent photochromism in a high concentration, a photochromic optical material, a process for producing the same and a molecular compound used in the material and process. More specifically, it relates to a photochromic composition having polymerization curability which can be suitably used to form a coating film having photochromism on the surface of an optical article such as a spectacle lens, or a photochromic composition which can provide an optical article such as a photochromic spectacle lens or film by curing a polymer component by cooling or removing an organic solvent, a photochromic optical material, a process for producing the same, and a molecular compound used in the material and the process.

DESCRIPTION OF THE PRIOR ART

Photochromism is a reversible phenomenon that a certain compound changes its color immediately upon exposure to light including ultraviolet rays and returns to its original color when it is placed in the dark by stopping exposure. A compound having this property is called "photochromic compound" and various compounds have been synthesized so far. Out of these photochromic compounds, chromene compounds have excellent durability and compounds which develop various colors such as yellow to light blue colors are known. Therefore, studies on these compounds are now being made aggressively.

For example, as a chromene compound having excellent physical properties, there are known a compound represented by the following formula (A) which develops a yellow color and is disclosed in the pamphlet of WO98/45281 and a compound represented by the following formula (B) which develops a blue color and is disclosed in the pamphlet of WO96/14596.

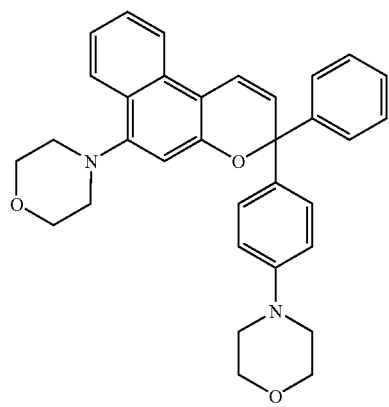

(A)

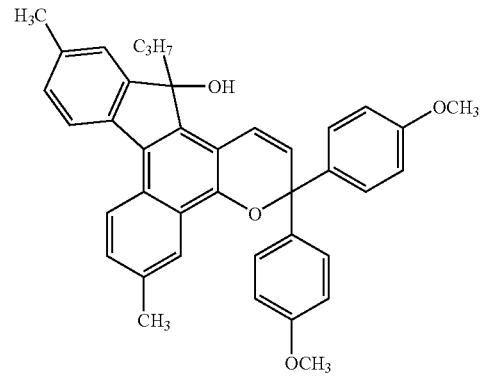

(B)

These chromene compounds are generally used for various purposes such as photochromic plastic lenses and coatings as a dispersion in a polymer matrix. As means of dispersing a chromene compound in a polymer matrix, there are known a method in which a thermosetting polymer matrix is impregnated with a chromene compound at a high temperature (WO96/14596) and a method in which a chromene compound is dissolved in a polymerizable monomer and then polymerized (WO97/48993).

However, in order to improve the photochromism of the above chromene compound, various substituents are introduced into the chromene compound, resulting in a great increase in its molecular weight. Therefore, the chromene compound does not diffuse in the polymer matrix smoothly or its solubility in a monomer becomes low, thereby making it difficult to disperse the chromene compound in the polymer matrix in a high concentration. For instance, when the chromene compound is dispersed by the above methods, the concentration of the chromene compound which can be dispersed is about 0.5 wt % and it is extremely difficult to disperse the chromene compound uniformly in a high concentration of more than 1 wt %. Therefore, a polymer obtained by dispersing the chromene compound in accordance with the above methods has a problem that the thickness of its coating film must be made large in order to obtain practical color development intensity. For example, when the polymer is used as a coating to form a thin film having a thickness of 0.1 mm or less, satisfactory color development intensity cannot be obtained.

Thus, there is unknown a method of dispersing uniformly a chromene compound having a polymer weight in a polymer matrix in a high concentration with ease.

SUMMARY OF THE INVENTION

It is a first object of the present invention to provide a photochromic composition which can dissolve a chromene compound in a high concentration.

It is a second object of the present invention to provide a photochromic optical material which is a cured product of a uniform dispersion containing a chromene compound in a polymer matrix in a high concentration.

It is a third object of the present invention to provide a curable composition which can easily and simply provide photochromism to an optical article by applying a curable composition as a coating agent which comprises the above chromene compound dissolved in a high concentration to the surface of an optical article such as a plastic lens and a process for producing the same.

It is a fourth object of the present invention to provide a molecular compound of a chromene compound and an aromatic compound and a process for producing the same.

Other objects and advantages of the present invention will become apparent from the following description.

According to the present invention, firstly, the above objects and advantages of the present invention are attained by a photochromic composition prepared by mixing together (1) 100 parts by weight of a radically polymerizable monomer or a polymer compound and (2) 0.01 to 20 parts by weight of a molecular compound of a chromene compound and an aromatic compound.

According to the present invention, secondly, the above objects and advantages of the present invention are attained by a coating composition comprising:

(1) 100 parts by weight of a radically polymerizable monomer;

(2) 1 to 30 parts by weight of a molecular compound of a chromene compound and an aromatic compound or a combination of this molecular compound and a photochromic compound; and (3) 0.01 to 10 parts by weight of a photopolymerization initiator, the number of parts by weight of the component being smaller than the number of parts by weight of the above component (2).

According to the present invention, thirdly, the above objects and advantages of the present invention are attained by a photochromic optical material which is a cured product of the curable composition of the present invention.

According to the present invention, in the fourth place, the above objects and advantages of the present invention are attained by a process for producing a photochromic optical material, comprising the step of curing the curable composition of the present invention.

According to the present invention, in the fifth place, the above objects and advantages of the present invention are attained by a photochromic optical material which comprises a substrate and a cured coating film of the above coating composition on at least one side of the substrate.

According to the present invention, in the sixth place, the above objects and advantages of the present invention are attained by a process for producing a photochromic optical material, which comprises applying the above coating composition to at least one side of a substrate; and curing the above coating composition by light or both light and heat.

Further, according to the present invention, in the seventh place, the above objects and advantages of the present invention are attained by a novel molecular compound of a chromene compound represented by the following formula (1) and an aromatic compound having a molecular weight of 70 to 150, the molecular compound being used for preparing composition of the present invention.

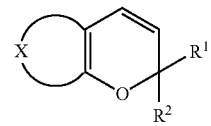

wherein $R^1$ and $R^2$ are each a substituted or non-substituted aryl group, or a substituted or non-substituted aromatic heterocyclic group, and the divalent group represented by the following formula (2) is a divalent condensed polycyclic organic group which has a benzene ring condensed to the 2H-pyran ring in the above formula (1) and may have a subsistent:

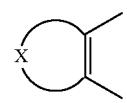

BRIEF DESCRIPTION OF THE DRAWINGS

FIG. 1 is a chart showing the proton nuclear magnetic resonance spectrum of a crystal (molecular compound) obtained in Example 1;

FIG. 2 is a chart showing the thermogram of a crystal (molecular compound) obtained in Example 1; and FIG. 3 is a chart showing the thermogram of a crystal obtained in Comparative Example 1.

DETAILED DESCRIPTION OF THE PREFERRED EMBODIMENT

The photochromic composition of the present invention is obtained by mixing together a radically polymerizable monomer or a polymer compound (to be referred to as "solvent for a molecular compound" hereinafter) and a molecular compound of a chromene compound. When a chromene compound is used in the form of a molecular compound, it can be dissolved easily in the above solvent for a molecular compound in a high concentration. The photochromic composition of the present invention can be cured by polymerization when the above solvent for a molecular compound is a radically polymerizable composition, by cooling when the above solvent for a molecular compound is, for example, a molten product of a polymer compound, or by removing a solvent for a polymer compound (also for the molecular compound) when the above solvent for a molecular compound is, for example, a solution of the polymer compound. The thus obtained cured product can be used as an optical article such as a spectacle lens or film having photochromism itself or a coating film for providing photochromism to various transparent substrates. The chromene compound can be existent in a solution state relatively stably without separating out from the obtained photochromic compound of the present invention. However, it is not confirmed whether the chromene compound is existent in the form of a molecular compound. The inventors of the present invention assume that the chromene compound does not need to be existent in the form of a molecular compound after dissolution and that bonding power between the chromene compound and the aromatic compound is weakened in part or all of the molecular compound although the chromene compound must be existent in the form of a molecular compound to promote its solubility.

The radically polymerizable monomer used in the photochromic composition of the present invention is not particularly limited and any known compound having a radically polymerizable group such as (meth)acryloyl group, (meth)acryloyloxy group, vinyl group, allyl group or styryl group may be used without any limitation. Out of these, compounds having a (meth) acryloyl group or (meth) acryloyloxy group as a radically polymerizable group are preferred from the viewpoint of easy acquisition and excellent curability.

In order to improve the chemical and mechanical properties such as solvent resistance, hardness and heat resistance, and photochromism such as color development intensity and fading speed of the cured product obtained after curing, a radically polymerizable monomer having a homopolymer L-scale Rockwell hardness of 60 or more (to be also referred to as "high-hardness monomer" hereinafter) and a radically polymerizable monomer having a homopolymer L-scale Rockwell hardness of 40 or less (to be also referred to as "low-hardness monomer" hereinafter) are preferably used in combination.

The L-scale Rockwell hardness is a hardness measured in accordance with JIS-B7726. It can be simply judged whether the monomer satisfies the above requirement for hardness by measuring the homopolymer of each monomer. Stated more specifically, as will be shown in Examples hereinafter, this can be easily confirmed by polymerizing a monomer to obtain a 2 mm-thick cured product, keeping it in a chamber maintained at 25° C. for 1 day and measuring its L-scale Rockwell hardness with a Rockwell hardness meter. In the polymer used to measure the above L-scale Rockwell hardness, 90% or more of polymerizable groups of the charged monomer must be polymerized. When 90% or more of the polymerizable groups are polymerized, the measured L-scale Rockwell hardness of the cured product is generally an almost constant value.

The above radically polymerizable monomer having a homopolymer L-scale Rockwell hardness of 60 or more (high-hardness monomer) has the effect of improving the solvent resistance, hardness and heat resistance of a cured product after curing. To make this effect more effective, a radically polymerizable monomer having a homopolymer L-scale Rockwell hardness of 65 to 130 is preferred.

The high-hardness monomer is a compound having preferably 2 to 15, more preferably 2 to 6 radically polymerizable groups in the molecule. Preferred examples of the high-hardness monomer include polymerizable monomers represented by the following formulas (3) to (7). When there is a range in the number of repetitions which can be taken by recurring units in the main chain in the polymerizable monomer represented by any one of these formulas, the polymerizable monomer may be a mixture of a plurality of molecules having different numbers of repetitions.

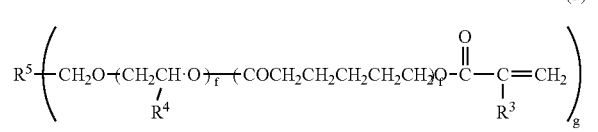

In the above formula, $R^3$ is a hydrogen atom or methyl group, $R^4$ is a hydrogen atom, methyl group or ethyl group, $R^5$ is a tervalent to hexavalent organic residual group, f is an integer of 0 to 3, f' is an integer of 0 to 3, and g is an integer of 3 to 6.

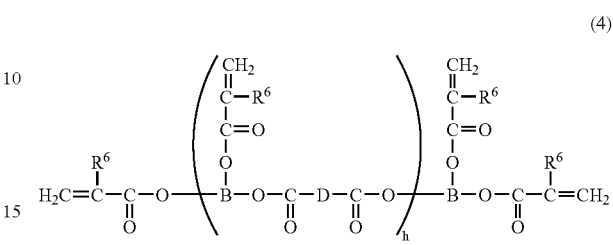

In the above formula, $R^6$ is a hydrogen atom or methyl group, B is a tervalent organic residual group, D is a divalent organic residual group, and h is an integer of 1 to 10.

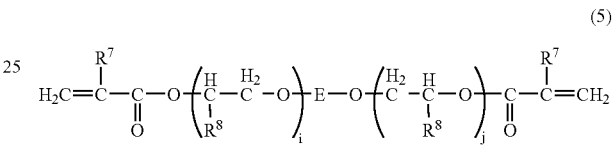

In the above formula, $R^7$ is a hydrogen atom or methyl group, $R^8$ is a hydrogen atom, methyl group, ethyl group or hydroxyl group, E is a divalent organic residual group containing a cyclic group, and i and j are each a positive integer or 0 which ensures that the average value of (i+j) is 0 to 6.

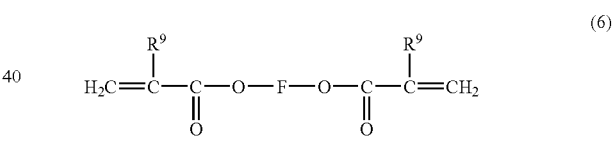

In the above formula, $R^9$ is a hydrogen atom or methyl group, and F is an alkylene group having 2 to 9 carbon atoms in the main chain which may have a side chain.

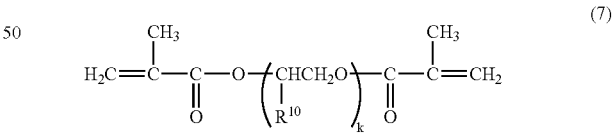

In the above formula, $R^{10}$ is a hydrogen atom, methyl group or ethyl group, and k is an integer of 1 to 6.

$R^3$, $R^6$, $R^7$ and $R^9$ in the above formulas (3) to (6) are each a hydrogen atom or methyl group. The compounds represented by the formulas (3) to (6) have 2 to 6 (meth) acryloyloxy groups. When a plurality of (meth)acryloyloxy groups are existent in one molecule, they may differ from one another but preferably are identical to one another from the viewpoint of easy acquisition (the same can be said of $R^{13}$ and $R^{14}$).

$R^4$ in the above formula (3) is a hydrogen atom, methyl group or ethyl group.

R⁵ in the formula (3) is a tervalent to hexavalent organic residual group. The organic residue is not particularly limited and may contain a bond other than a carbon-carbon bond, such as an ester bond, ether bond, amide bond, thioether bond, sulfonyl bond or urethane bond in the main chain. To obtain a homopolymer L-scale Rockwell hardness of 60 or more, R⁵ is preferably an organic residual group having 1 to 30 carbon atoms, more preferably an organic residual group having 1 to 15 carbon atoms which may contain an ether bond and/or an urethane bond.

Further, f and f' are each independently an integer of 0 to 3. When f are f' are larger than 3, these monomers tend to have a homopolymer L-scale Rockwell hardness of less than 60. To obtain an L-scale Rockwell hardness of 60 or more, the total of f and f' is preferably 0 to 3.

Illustrative examples of the high-hardness monomer represented by the formula (3) include trimethylolpropane trimethacrylate, trimethylolpropane triacrylate, tetramethylolmethane trimethacrylate, tetramethylolmethane triacrylate, trimethylolpropane trimethacrylate, tetramethylolmethane tetramethacrylate, tetramethylolmethane tetraacrylate, trimethylolpropane triethylene glycol trimethacrylate, trimethylolpropane triethylene glycol triacrylate, ethoxylated pentaerythritol tetraacrylate, ethoxylated pentaerythritol tetramethacrylate, pentaerythritol trimethacrylate, pentaerythritol tetramethacrylate, dipentaerythritol hexaacrylate, urethane oligomer tetraacrylate, urethane oligomer hexamethacrylate, urethane oligomer hexaacrylate, polyester oligomer hexaacrylate, caprolactone modified dipentaerythritol hexaacrylate and ditrimethylolpropane tetraacrylate.

B in the above formula (4) is a tervalent organic residual group and D is a divalent organic residual group. B and D are not particularly limited and may contain a bond other than a carbon-carbon bond, such as an ester bond, ether bond, amide bond, thioether bond, sulfonyl bond or urethane bond in the main chains thereof. To obtain a homopolymer L-scale Rockwell hardness of 60 or more, B is preferably an organic residual group derived from a linear or branched hydrocarbon having 3 to 10 carbon atoms, and D is preferably an organic residual group derived from a linear or branched aliphatic hydrocarbon having 1 to 10 carbon atoms or an aromatic hydrocarbon having 6 to 10 carbon atoms.

To obtain a homopolymer L-scale Rockwell hardness of 60 or more, h is an integer of 1 to 10, preferably 1 to 6.

Illustrative examples of the high-hardness monomer represented by the formula (4) include a tetrafunctional polyester oligomer having a molecular weight of 2,500 to 3,500 (EB80 of Daicel UCB Co., Ltd., etc.), tetrafunctional polyester oligomer having a molecular weight of 6,000 to 8,000 (EB450 of Daicel UCB Co., Ltd., etc.), hexagonal polyester oligomer having a molecular weight of 45,000 to 55,000 (EB1830 of Daicel UCB Co., Ltd., etc.) and tetrafunctional polyester oligomer having a molecular weight of 10,000 (GX8488B of Dai-ichi Kogyo Seiyaku, Co., Ltd., etc.).

R⁸ in the above formula (5) is a hydrogen atom, methyl group, ethyl group or hydroxyl group.

E in the above formula (5) is a divalent organic residual group having a cyclic group. The organic residual group is not particularly limited if it contains a cyclic group and may contain a bond other than a carbon-carbon bond, such as an ester bond, ether bond, amide bond, thioether bond, sulfonyl bond or urethane bond in the main chain. The cyclic group contained in E is a benzene ring, cyclohexane ring, adamantane ring or cyclic group shown below.

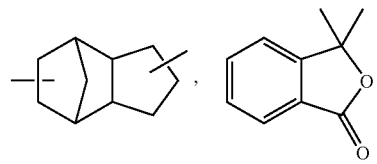

The cyclic group contained in E is preferably a benzene ring and E is more preferably a group represented by the following formula:

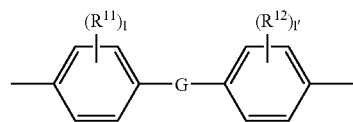

wherein G is an oxygen atom, sulfur atom, or a group selected from the group consisting of —S(O₂)—, —C(O)—, —CH₂—, —CH=CH—, —C(CH₃)₂— and —C(CH₃)(C₆H₅)—, R¹¹ and R¹² are each independently an alkyl group having 1 to 4 carbon atoms or halogen atom, and l and l' are each independently an integer of 0 to 4.

E is the most preferably a group represented by the following formula.

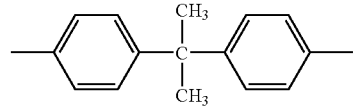

In the formula (5), i and j are each a positive integer or 0 which ensures that the average value of (i+j) is 0 to 6. The compound represented by the formula (5) is generally obtained as a mixture of a plurality of compounds which differ from one another in i and j excluding the case where i and j are both "0". Since it is difficult to isolate these compounds, i and j are expressed by the average value of (i+j). The average value of (i+j) is preferably 2 to 6.

Illustrative examples of the compound represented by the formula (5) include bisphenol A dimethacrylate, 2,2-bis(4-methacryloyloxyethoxyphenyl)propane and 2,2-bis(3,5-dibromo-4-methacryloyloxyethoxyphenyl) propane.

In the above formula (6), R⁹ is a hydrogen atom or methyl group, and F is an alkylene group having 2 to 9 carbon atoms in the main chain, which may have a side chain. Examples of the alkylene group having 2 to 9 carbon atoms in the main chain include ethylene group, propylene group, trimethylene group, butylene group, neopentylene group, hexylene group and nonylene group. When the number of carbon atoms in the main chain is larger than 9, the homopolymer L-scale Rockwell hardness of the obtained compound tends not to be 60 or more.

Illustrative examples of the compound represented by the formula (6) include ethylene glycol diacrylate, ethylene glycol dimethacrylate, 1,4-butylene glycol dimethacrylate, 1,9-nonylene glycol dimethacrylate, neopentylene glycol dimethacrylate and neopentylene glycol diacrylate.

In the above formula (7), R¹⁰ is a hydrogen atom, methyl group or ethyl group, and k is an integer of 1 to 6. When k is larger than 6, the homopolymer L-scale Rockwell hardness of the obtained compound tends not to be 60 or more, and k is preferably 3 or 4.

Illustrative examples of the compound represented by the formula (7) include diethylene glycol dimethacrylate, triethylene glycol dimethacrylate, tetraethylene glycol dimethacrylate, tripropylene glycol dimethacrylate and tetrapropylene glycol dimethacrylate.

These radically polymerizable monomers having a homopolymer L-scale Rockwell hardness of 60 or more may be used alone or in combination of two or more.

Among the compounds represented by the above formulas (3) to (7) are compounds having a homopolymer L-scale Rockwell hardness of less than 60 according to a combination of substituents. The compounds are classified into a group of low-hardness monomers or medium-hardness monomers described after.

There are high-hardness monomers which are not represented by the above formulas (3) to (7). Typical examples of the above monomers include bisphenol A diglycidyl methacrylate, ethylene glycol bisglycidyl methacrylate and glycidyl methacrylate.

The curable composition of the present invention preferably comprises a low-hardness monomer having a homopolymer L-scale Rockwell hardness of 40 or less, in addition to the above high-hardness monomer.

The low-hardness monomer has the effect of making the cured product strong and improving the fading speed of the photochromic compound.

The low-hardness monomer is a bifunctional monomer represented by the following formula (8):

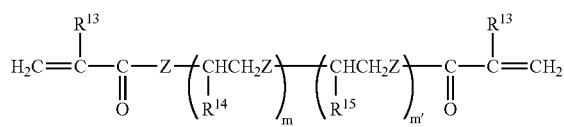

wherein $R^{13}$ is a hydrogen atom or methyl group, $R^{14}$ and $R^{15}$ are each independently a hydrogen atom, methyl group or ethyl group, Z is an oxygen atom or sulfur atom, m is an integer of 1 to 70 when $R^{13}$ is a hydrogen atom and an integer of 7 to 70 when $R^{13}$ is a methyl group, and m' is an integer of 0 to 70, or the following formula (9):

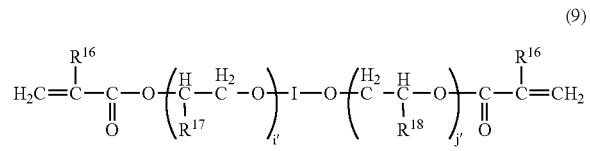

wherein $R^{16}$ is a hydrogen atom or methyl group, $R^{17}$ and $R^{18}$ are each independently a hydrogen atom, methyl group, ethyl group or hydroxyl group, I is a divalent organic residual group having a cyclic group, and i' and j' are each an integer which ensures that the average value of (i'+j') becomes 8 to 40, or a monofunctional monomer represented by the following formula (10):

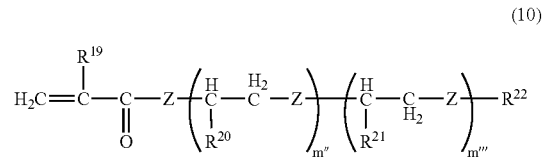

wherein $R^{19}$ is a hydrogen atom or methyl group, $R^{20}$ and $R^{21}$ are each independently a hydrogen atom, methyl group or ethyl group, $R^{22}$ is a hydrogen atom, alkyl group, alkenyl group, alkoxyalkyl group or haloalkyl group having 1 to 25 carbon atoms, aryl group having 6 to 25 carbon atoms or acyl group other than a (meth)acryloyl group having 2 to 25 carbon atoms, Z is an oxygen atom or sulfur atom, m" is an integer of 1 to 70 when $R^{19}$ is a hydrogen atom and an integer of 4 to 70 when $R^{19}$ is a methyl group, and m'" is an integer of 0 to 70, or the following formula (11):

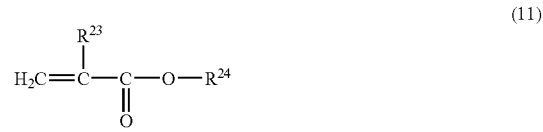

wherein $R^{23}$ is a hydrogen atom or methyl group, $R^{24}$ is an alkyl group having 1 to 20 carbon atoms when $R^{23}$ is a hydrogen atom and an alkyl group having 8 to 40 carbon atoms when $R^{23}$ is a methyl group.

In the above formulas (8) to (11), $R^{13}$, $R^{16}$, $R^{19}$ and $R^{23}$ are each a hydrogen atom or methyl group. That is, the low-hardness monomer generally has two or less (meth)acryloyloxy groups or (meth)acryloylthio groups as a polymerizable group.

In the above formula (8), $R^{14}$ and $R^{15}$ are each independently a hydrogen atom, methyl group or ethyl group, and Z is an oxygen atom or sulfur atom.

In the formula (8), when $R^{13}$ is a hydrogen atom, that is, the low-hardness monomer has an acryloyloxy group or acryloylthio group as a polymerizable group, m is an integer of 7 to 70 and when $R^{13}$ is a methyl group, that is, the low-hardness monomer has a methacryloyloxy group or methacryloylthio group as a polymerizable group, m is an integer of 1 to 70. Further, m' is an integer of 0 to 70.

Illustrative examples of the low-hardness monomer represented by the above formula (8) include alkylene glycol di(meth)acrylates such as trialkylene glycol diacrylate, tetraalkylene glycol diacrylate, nonylalkylene glycol diacrylate and nonylalkylene glycol dimethacrylate.

$R^{16}$ in the above formula (9) is a hydrogen atom, methyl group or ethyl group. I is a divalent organic residual group having a cyclic group. I is identical to E having a cyclic group in the above formula (5). i' and j' in the formula (9) are each an integer which ensures that the average value of (i'+j') is 8 to 40, preferably 9 to 30. i' and j' are generally expressed by the average value for the same reason as i and j in the above formula (5).

Illustrative examples of the low-hardness monomer represented by the formula (9) include 2,2-bis(4-acryloyloxypolyethylene glycol phenyl)propane having an average molecular weight of 776.

In the above formula (10), $R^{19}$ is a hydrogen atom or methyl group, and $R^{20}$ and $R^{21}$ are each independently a hydrogen atom, methyl group or ethyl group. $R^{22}$ is a hydrogen atom, alkyl group, alkenyl group, alkoxyalkyl group or haloalkyl group having 1 to 25 carbon atoms, aryl group having 6 to 25 carbon atoms or acyl group other than a (meth)acryloyl group having 2 to 25 carbon atoms.

Examples of the alkyl group or alkenyl group having 1 to 25 carbon atoms include methyl group, ethyl group, propyl group and nonyl group. These alkyl groups or alkenyl groups may be linear or branched and further may be substituted by a substituent such as a halogen atom, hydroxyl group, aryl group or epoxy group.

Examples of the alkoxyalkyl group having 1 to 25 carbon atoms include methoxybutyl group, ethoxybutyl group, butoxybutyl group and methoxynonyl group.

Examples of the aryl group having 6 to 25 carbon atoms include phenyl group, toluyl group, anthranyl group or octylphenyl group. Examples of the acyl group other than a (meth)acryloyl group include acetyl group, propionyl group, butyryl group, valeryl group and oleyl group.

In the formula (10), m" is an integer of 1 to 70 when $R^{19}$ is a hydrogen atom, that is, the low-hardness monomer has an acryloyloxy group or acryloylthio group as a polymerizable group and an integer of 4 to 70 when $R^{19}$ is a methyl group, that is, the low-hardness monomer has a methacryloyloxy group or methacryloylthio group as a polymerizable group. Further, m'" is an integer of 0 to 70.

Illustrative examples of the low-hardness monomer represented by the formula (10) include polyalkylene glycol (meth)acrylates such as polyethylene glycol methacrylate having an average molecular weight of 526, polyethylene glycol methacrylate having an average molecular weight of 360, methyl ether polyethylene glycol methacrylate having an average molecular weight of 475, methyl ether polyethylene glycol methacrylate having an average molecular weight of 1,000, polypropylene glycol methacrylate having an average molecular weight of 375, polypropylene methacrylate having an average molecular weight of 430, polypropylene methacrylate having an average molecular weight of 622, methyl ether polypropylene glycol methacrylate having an average molecular weight of 620, polytetramethylene glycol methacrylate having an average molecular weight of 566, octylphenyl ether polyethylene glycol methacrylate having an average molecular weight of 2,034, nonylether polyethylene glycol methacrylate having an average molecular weight of 610, methyl ether polyethylene thioglycol methacrylate having an average molecular weight of 640 and perfluoroheptyl ethylene glycol methacrylate having an average molecular weight of 498.

In the above formula (11), $R^{23}$ is a hydrogen atom or methyl group, and $R^{24}$ is an alkyl group having 1 to 20 carbon atoms when $R^{23}$ is a hydrogen atom and an alkyl group having 8 to 40 carbon atoms when $R^{23}$ is a methyl group.

These alkyl groups may be linear or branched and further may be substituted by a substituent such as halogen atom, hydroxyl group, alkoxyl group, acyl group or epoxy group.

Illustrative examples of the low-hardness monomer represented by the formula (11) include stearyl methacrylate, lauryl methacrylate, ethylhexyl methacrylate, methyl acrylate, ethyl acrylate, butyl acrylate and lauryl acrylate.

Out of the low-hardness monomers represented by the above formulas (8) to (11), methyl ether polyethylene glycol methacrylate having an average molecular weight of 475, methyl ether polyethylene glycol methacrylate having an average molecular weight of 1,000, trialkylene glycol diacrylate, tetraalkylene glycol diacrylate, nonylalkylene glycol diacrylate, methyl acrylate, ethyl acrylate, butyl acrylate and lauryl acrylate are particularly preferred.

These radically polymerizable monomers having a homopolymer L-scale Rockwell hardness of 40 or less may be used alone or in combination of two or more.

Among the compounds represented by the above formulas (8) to (11) are compounds having a homopolymer L-scale Rockwell hardness of 40 or more according to a combination of substituents. These compounds are classified as high-hardness monomers described above or medium-hardness monomers which will be described hereinafter.

In the composition of the present invention, a monomer which is neither a high-hardness monomer nor a low-hardness monomer described above, that is, a monomer having a homopolymer L-scale Rockwell hardness of more than 40 and less than 60 (to be also referred to as "medium-hardness monomer") may be used. Examples of the medium-hardness monomer include bifunctional (meth)acrylates such as polytetramethylene glycol dimethacrylate having an average molecular weight of 650, polytetramethylene glycol dimethacrylate having an average molecular weight of 1,400, and bis (2-methacryloyloxyethylthioethyl) sulfide; polyallyl compounds such as diallyl phthalate, diallyl isophthalate, diallyl tartarate, diallyl epoxysuccinate, diallyl fumarate, diallyl chlorendate, diallyl hexaphthalate and allyl diglycol carbonate; polythioacrylic and polythiomethacrylic acid ester compounds such as 1,2-bis(methacryloylthio)ethane, bis(2-acryloylthioethyl)ether and 1,4-bis(methacryloylthiomethyl)benzene; unsaturated carboxylic acids such as acrylic acid, methacrylic acid and maleic anhydride; acrylic and methacrylic acid ester compounds such as methyl methacrylate, butyl methacrylate, benzyl methacrylate, phenyl methacrylate, 2-hydroxyethyl methacrylate and biphenyl methacrylate; fumaric acid ester compounds such as diethyl fumarate and diphenyl fumarate; thioacrylic and thiomethacrylic acid ester compounds such as methyl thioacrylate, benzyl thioacrylate and benzyl thiomethacrylate; vinyl compounds such as styrene, chlorostyrene, methylstyrene, vinylnaphthalene, α-methylstyrene dimmer, bromostyrene, divinylbenzene and vinylpyrrolidone; and radically polymerizable monofunctional monomers such as (meth)acrylates whose hydrocarbon chain having an unsaturated bond in the molecule has 6 to 25 carbon atoms, exemplified by oleyl methacrylate, nerol methacrylate, geraniol methacrylate, linalool methacrylate and farnesol methacrylate.

The above high-hardness monomer, low-hardness monomer and medium-hardness monomer may be suitably mixed together before use. In order to well balance the characteristic properties such as solvent resistance, hardness and heat resistance, or photochromic properties such as color development intensity and fading speed of a cured product of the curable composition, it is preferred that a low-hardness monomer be contained in an amount of 5 to 70 wt % and a high-hardness monomer be contained in an amount of 5 to 95 wt % based on the total of all the radically polymerizable monomers. Particularly preferably, a monomer having three or more radically polyemrizable groups is contained as the high-hardness monomer in an amount of at least 5 wt % based on the total of all the radically polymerizable monomers.

The radically polymerizable monomers of the present invention preferably include a radically polymerizable monomer having at least one epoxy group and at least one radically polymerizable group in the molecule (to be simply referred to as "epoxy-based monomer" hereinafter) besides the above monomers classified by hardness. The epoxy-based monomer may have a homopolymer L-scale Rockwell hardness of 60 or more or 40 or less based on its structure. It is classified as a high-hardness monomer, low-hardness monomer or medium-hardness monomer according to the hardness of its homopolymer.

By using the epoxy-based monomer as one of the radically polymerizable monomers in the present invention, the durability of the photochromic compound can be improved and further the adhesion of the photochromic compound can be improved when it is used as a coating composition.

Known compounds may be used as the epoxy-based monomer but compounds having a (meth)acryloyloxy group as a radically polymerizable group are preferred.

A monomer preferably used as the epoxy-based monomer is represented by the following formula (12):

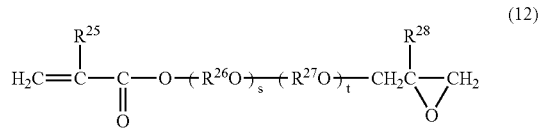

(12)

wherein $R^{25}$ and $R^{28}$ are each independently a hydrogen atom or methyl group, $R^{26}$ and $R^{27}$ are each independently an alkylene group having 1 to 4 carbon atoms or a group represented by the following formula, and s and t are each independently an integer of 0 to 10,

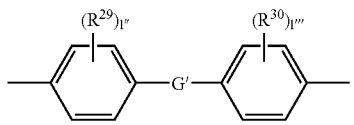

wherein G' is an oxygen atom, sulfur atom or group selected from the group consisting of —S(O$_2$)—, —C(O)—, —CH$_2$—, —CH═CH—, —C(CH$_3$)$_2$— and —C(CH$_3$)(C$_6$H$_5$)—, $R^{29}$ and $R^{30}$ are each independently an alkyl group having 1 to 4 carbon atoms or halogen atom, and 1" and 1'" are each independently an integer of 0 to 4.

Examples of the alkylene group having 1 to 4 carbon atoms represented by $R^{26}$ and $R^{27}$ include methylene group, ethylene group, propylene group, trimethylene group and butylene group. These alkylene groups may be substituted by a hydroxyl group or halogen atom.

When $R^{26}$ and/or $R^{27}$ are/is a group represented by the following formula, G' is an oxygen atom, sulfur atom or group selected from the group consisting of —S(O$_2$)—, —C(O)—, —CH$_2$—, —CH═CH—, —C(CH$_3$)$_2$— and —C(CH$_3$)(C$_6$H$_5$)—, $R^{29}$ and $R^{30}$ are each independently an alkyl group having 1 to 4 carbon atoms, such as methyl group, ethyl group, propyl group or butyl group, or halogen atom such as chlorine atom or bromine atom, and 1" and 1'" are each independently an integer of 0 to 4.

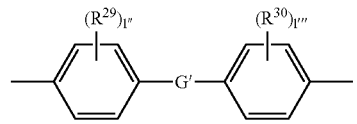

The group represented by the above formula is the most preferably a group represented by the following formula.

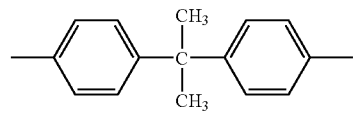

Illustrative examples of the epoxy-based monomer represented by the above formula (12) include glycidyl acrylate, glycidyl methacrylate, β-methylglycidyl methacrylate, bisphenol A-monoglycidyl ether-methacrylate, 4-glyhcidyloxy methacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate and glycidyloxy polyethylene glycol methacrylate having an average molecular weigh of 540. Out of these, glycidyl acrylate, glycidyl methacrylate and glycidyloxy polyethylene glycol methacrylate having an average molecular weight of 540 are particularly preferred.

The amount of the epoxy-based monomer is preferably 0.01 to 30 wt %, particularly preferably 0.1 to 20 wt % based on the total of all the radically polymerizable monomers.

The curable composition of the present invention may further comprise a radically polymerizable monomer having a silanol group or a group which forms a silanol group through hydrolysis (may be referred to as "silyl monomer" hereinafter) or a radically polymerizable monomer having an isocyanate group (may be referred to as "isocyanate monomer" hereinafter) to improve the hard coating properties of a cured coating film or adhesion between a cured coating film and a substrate such as a spectacle lens when the composition is used as a coating.

Any known compound having a silanol group (≡Si—OH) or a group which forms a silanol group through hydrolysis and a radically polymerizable group may be used as the silyl monomer.

Examples of the group which forms a silanol group through hydrolysis include alkoxysilyl group (≡Si—O—R; R is an alkyl group), aryloxysilyl group (≡Si—O—Ar; Ar is an aryl group which may be substituted), halosilyl group (≡Si—X; X is a halogen atom) and silyloxysilyl group (disiloxane bond; ≡Si—O—Si≡).

Out of the above groups which form a silanol group through hydrolysis, alkoxysilyl group and silyloxysilyl group are preferred, alkoxysilyl group including an alkoxyl group having 1 to 4 carbon atoms is more preferred, and methoxysilyl group and ethoxysilyl group are the most preferred because a silanol group is easily formed, synthesis and preservation are easy and a group eliminated from a silicon atom by a reaction has little influence upon the physical properties of the cured product.

Examples of the radically polymerizable group include known radically polymerizable groups such as (meth)acryloyl group, (meth)acryloyl group derivatives such as (meth)acryloyloxy group, (meth)acryloylamino group and (meth)

acryloylthio group, vinyl group, allyl group and styryl group. When the radically polymerizable group is a vinyl group, allyl group or styryl group, it may have a substituent. Examples of the substituent include alkyl groups and haloalkyl groups having 1 to 4 carbon atoms such as methyl group, ethyl group, propyl group, butyl group, chloromethyl group and trifluoromethyl group, halogen atom, cyano group, nitro group and hydroxyl group. When the radically polymerizable group is a (meth)acryloylamino group, an organic group such as substituted or nonsubstituted alkyl group, aryl group or allyl group may be bonded to the amidonitrogen atom of the group, in addition to a (meth) acryloyl group and the above silanol group or group which forms a silanol group through hydrolysis.

Out of the radically polymerizable groups, (meth)acryloyl group and (meth)acryloyloxy group are preferred, and (meth)acryloyloxy group is more preferred from the viewpoints of easy acquisition and high polymerizability.

Preferred silyl monomers having the group capable of forming a silanol group through hydrolysis and a radically polymerizable group are represented by the following formulas (13) to (15):

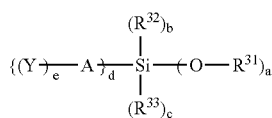
(13)

wherein $R^{31}$ is an alkyl group or aryl group, $R^{32}$ and $R^{33}$ are each independently an alkyl group, aryl group or acyl group, A is a divalent to tetravalent organic residual group, Y is a radically polymerizable group, a is an integer of 1 to 3, b is an integer of 0 to 2, c is an integer of 0 to 2, d is an integer of 1 to 3, and e is an integer of 1 to 3, with the proviso that (a+b+c+d)=4,

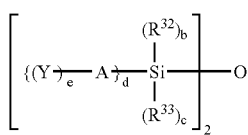
(14)

wherein $R^{32}$ and $R^{33}$ are each independently an alkyl group, aryl group or acyl group, A is a divalent to tetravalent organic residual group, Y is a radically polymerizable group, b is an integer of 0 to 2, c is an integer of 0 to 2, d is an integer of 1 to 3, and e is an integer of 1 to 3, with the proviso that (b+c+d)=3,

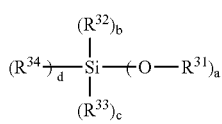
(15)

wherein $R^{31}$ is an alkyl group or aryl group, $R^{32}$ and $R^{33}$ are each independently an alkyl group, aryl group or acyl group, $R^{34}$ is a vinyl group, a is an integer of 1 to 3, b is an integer of 0 to 2, c is an integer of 0 to 2, and d is an integer of 1 to 3, with the proviso that (a+b+c+d)=4.

In the above formulas (13) and (15), $R^{31}$ is an alkyl group or aryl group. It is preferably an alkyl group having 1 to 10 carbon atoms in the main chain or an aryl group having 6 to 10 carbon atoms as members of a ring because they can easily form a silanol group through hydrolysis and have keeping stability. The alkyl group or aryl group may have a substituent. Examples of the substituent include alkyl groups having 1 to 10 carbon atoms such as methyl group, ethyl group and propyl group, haloalkyl groups having 1 to 10 carbon atoms such as chloromethyl group and trifluoromethyl group, alkoxyl groups having 1 to 10 carbon atoms such as methoxy group, ethoxy group and butoxy group, acyl groups having 2 to 10 carbon atoms such as acetyl group, propionyl group, oleyl group and benzoyl group, amino group, alkyl-substituted amino groups having 1 to 10 carbon atoms such as methylamino group, ethylamino group, dimethylamino group and diethylamino group, halogen atoms such as fluorine atom, chlorine atom and bromine atom, hydroxyl group, carboxyl group, mercapto group, cyano group and nitro group.

Examples of the substituted or nonsubstituted alkyl group having 1 to 10 carbon atoms in the main chain include methyl group, ethyl group, propyl group, butyl group and chloromethyl group. Examples of the substituted or nonsubstituted aryl group having 6 to 10 carbon atoms as members of a ring include phenyl group, toluyl group and xylyl group.

$R^{31}$ is preferably an alkyl group, more preferably an alkyl group having 1 to 4 carbon atoms, the most preferably methyl group or ethyl group from the viewpoints of formation ease of a silanol group through hydrolysis and keeping stability.

In the above formulas (13) to (15), $R^{32}$ and $R^{33}$ are each independently an alkyl group, aryl group or acyl group. Examples of the alkyl group and aryl group are the same as those listed for $R^1$ and preferred examples thereof are the same as those listed for $R^1$. The acyl group is preferably an acyl group having 2 to 10 carbon atoms. The acyl group may be an aliphatic acyl group or aromatic acyl group. Examples of the acyl group include acetyl group, propionyl group and benzoyl group.

In the above formulas (13) and (14), A is a divalent to tetravalent organic residual group, preferably a divalent to tetravalent organic residual group having 1 to 30 carbon atoms. The organic residual group is not limited to a particular structure and may have a side chain or a substituent. It also may have a bond other than a carbon-carbon bond, such as ether bond, ester bond, amide bond, amino bond, urethane bond, thioether bond or sulfonyl bond in the structure and may further contain an oxo group (ketone carbon). Preferred examples of the substituent of the organic residual group include halogen atoms such as fluorine atom, chlorine atom and bromine atom, hydroxyl group, amino group, mercapto group, cyano group and nitro group.

The organic residual group is preferably an organic residual group having 1 to 10 carbon atoms, as exemplified by alkylene groups having 1 to 10 carbon atoms such as methylene group, ethylene group, propylene group, trimethylene group and butylene group, alkylenedioxy groups having 1 to 10 carbon atoms such as methylenedioxy group, ethylenedioxy group, propylenedioxy group and butylenedioxy group, and groups shown below (in the below formulas, n is an integer of 1 to 5, and n' and n" are each an integer of 1 to 3).

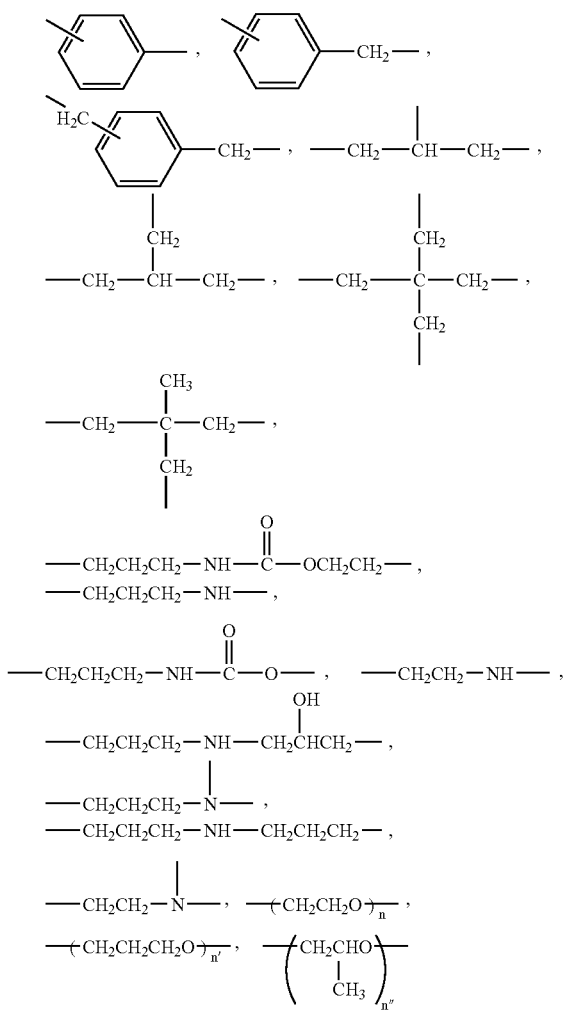

What are obtained by substituting these groups by the above substituent may also be used as the organic residual group.

Y in the above formulas (13) and (14) is a radically polymerizable group selected from (meth)acryloyl group, (meth)acryloyl group derivatives such as (meth)acryloyloxy group, (meth)acryloylamino group and (meth)acryloylthio group, substituted and nonsubstituted vinyl groups, substituted and nonsubstituted allyl groups, and substituted and nonsubstituted styryl groups. It is preferably a (meth)acryloyl group or (meth)acryloyloxy group.

Out of the silyl monomers represented by the above formulas, silyl monomers represented by the formula (13) are preferred, and silyl monomers represented by following formula (16) are particularly preferred:

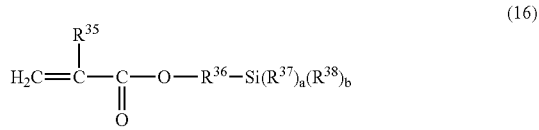

(16)

wherein $R^{35}$ is a hydrogen atom or methyl group, $R^{36}$ is an alkylene group having 1 to 10 carbon atoms, $R^{37}$ is an alkoxyl group having 1 to 4 carbon atoms, $R^{38}$ is an alkyl group having 1 to 4 carbon atoms, a is an integer of 1 to 3, and b is an integer of 0 to 2, with the proviso that (a+b)=3.

Examples of the alkylene group having 1 to 10 carbon atoms represented by $R^{35}$ in the above formula (16) include ethylene group, propylene group, trimethylene group and butylene group. Examples of $R^{37}$ include methoxy group, ethoxy group, propoxy group and butoxy group. Examples of $R^{38}$ include methyl group, ethyl group, propyl group and butyl group.

Illustrative examples of the silyl monomers represented by the above formulas (13) to (15) include γ-methacryloyloxypropyltrimethoxysilane, γ-methacryloyloxypropyltriethoxysilane, γ-methacryloyloxypropylmethyldimethoxysilane, (3-acryloxypropyl)dimethylmethoxysilane, (3-acryloxypropyl)methyldimethoxysilane, (3-acryloxypropyl)trimethoxysilane, 3-(N-allylamino)propyltrimethoxysilane, allyldimethoxysilane, allyltriethoxysilane, allyltrimethoxysilane, 3-aminophenoxydimethylvinylsilane, 4-aminophenoxydimethylvinylsilane, 3-(3-aminopropoxy)-3,3-dimethyl-1-propenyltrimethoxysilane, butenyltriethoxysilane, 2-(chloromethyl)allyltrimethoxysilane, diethoxyvinylsilane, 1,3-divinyltetraethoxydisiloxane, docosenyltriethoxysilane, o-(methacryloxyethyl)-N-(triethoxysilylpropyl)urethane, N-(3-methacryloxy-2-hydroxypropyl)-3-aminopropyltriethoxysilane, methacryloxyethoxytrimethylsilane, (methacryloxymethyl)dimethylethoxysilane, methacryloxymethyltriethoxysilane, methacryloxymethyltrimethoxysilane, methacryloxypropyldimethylethoxysilane, methacryloxypropyldimethylmethoxysilane, methacryloxypropyltris(methoxyethoxy)silane, 7-octenyltrimethoxysilane, 1,3-bis(methacryloxy)-2-trimethylsiloxypropane, tetrakis(2-methacryloxyethoxy)silane, trivinylethoxysilane, trivinylmethoxysilane, vinyldimethylethoxysilane, vinyldiphenylethoxysilane, vinylmethyldiacetoxysilane, vinylmethyldiethoxysilane, vinylmethyldimethoxysilane, o-(vinyloxyethyl)-N-(triethoxysilylpropyl)urethane, vinyloxytrimethylsilane, vinylphenyldiethoxysilane, vinylphenylmethylmethoxysilane, vinyltriacetoxysilane, vinyltri-t-butoxysilane, vinyltriethoxysilane, vinyltriisopenoxysilane, vinyltriisopropoxysilane, vinyltrimethoxysilane, vinyltriphenoxysilane and vinyltris(2-methoxyethoxy)silane.

Out of these, silyl monomers represented by the above formula (16) such as γ-methacryloyloxypropyltrimethoxysilane, γ-methacryloyloxypropyltriethoxysilane, γ-methacryloyloxypropylmethyldimethoxysilane, (3-acryloxypropyl)dimethylmethoxysilane, (3-acryloxypropyl)methyldimethoxysilane, (3-acryloxypropyl)trimethoxysilane, (methacryloxymethyl)dimethylethoxysilane, methacryloxymethyltriethoxysilane, methacryloxymethyltrimethoxysilane, methacryloxypropyldimethylethoxysilane and methacryloxypropyldimethylmethoxysialne are particularly preferred.

In the present invention, adhesion to a substrate and a hard coat material can be improved by using an isocyanate monomer in place of the above silyl monomer.

Any known compound having an isocyanate group (—NCO) and a radically polymerizable group may be used as the isocyanate monomer.

The isocyanate monomer may be represented by the following formula (17) or (18):

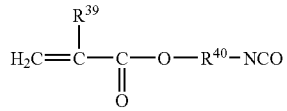

(17)

wherein $R^{39}$ is a hydrogen atom or methyl group, and $R^{40}$ is an alkylene group,

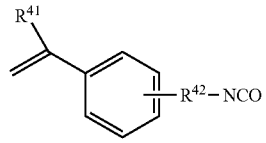

(18)

wherein $R^{41}$ is a hydrogen atom or methyl group, and $R^{42}$ is an alkylene group.

In the above formulas (17) and (18), $R^{40}$ and $R^{42}$ are both an alkylene group. The alkylene group is preferably an alkylene group having 1 to 10 carbon atoms. Examples of the alkylene group include methylene group, ethylene group, propylene group, trmiethylene group and butylene group.

Preferred examples of the isocyanate monomer include 2-isocyanatoethoxymethacrylate and 4-(2-isocyanatoisopropyl)styrene.

The amount of the silyl monomer or isocyanate monomer in the present invention is not particularly limited. However, when the above monomer is added to improve adhesion to a substrate such as a spectacle lens and a hard coat material, its amount is preferably 0.5 to 20 wt %, more preferably 1 to 10 wt % based on the total of all the radically polymerizable monomers so as to improve scratching resistance at the time of forming a hard coat or photochromism such as color development intensity or fading speed.

These silyl monomers or isocyanate monomers may be used alone or in combination of two or more. Also, a mixture of a silyl monomer and an isocyanate monomer may be used.

When a silyl monomer or isocyanate monomer is to be added to the radically polymerizable monomers, an amine compound is preferably added as a catalyst besides the radically polymerizable monomers. By adding an amine compound, when the obtained composition is used as the curable composition or coating composition of the present invention, adhesion between a cured coating layer of the curable composition or coating composition and a hard coat layer or a substrate can be greatly improved.

Any known basic amine compound can be used as the amine compound used in the present invention if it serves as a condensation or addition catalyst for the above silyl monomer or isocyanate monomer. However, hindered amine compounds having an amino group represented by the following formula as the sole amino group are excluded because they don't have the above catalytic function:

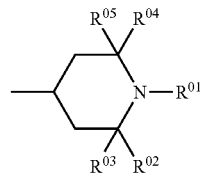

wherein $R^{01}$ is a hydrogen atom or alkyl group, $R^{02}$, $R^{03}$, $R^{04}$ and $R^{05}$ are the same or different alkyl groups.

Preferred examples of the amine compound which can be suitably used in the present invention include nonpolymerizable low-molecular amine compounds such as triethanolamine, N-methyldiethanolamine, triisopropanolamine, 4,4-dimethylaminobenzophenone and diazabicyclooctane, amine compounds having a polymerizable group such as N,N-dimethylaminoethyl methacrylate and N,N-diethylaminoethyl methacrylate, and amine compounds having a silyl group such as n-(hydroxyethyl)-N-methylaminopropyltrimethoxysilane, dimethoxyphenyl-2-piperidinoethoxysilane, N,N-diethylaminomethyltrimethylsilane and (N,N-diethyl-3-aminopropyl)trimethoxysilane.

Out of the above preferred amine compounds, amine compounds having a hydroxyl group, (meth)acryloyloxy group as a radically polymerizable group or group capable of forming a silanol group through hydrolysis are preferred from the viewpoint of the improvement of adhesion. For example, amine compounds represented by the following formula (19) are preferred because they have high basicity and a high adhesion improving effect:

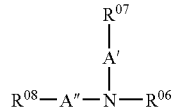

(19)

wherein $R^{06}$ is a hydrogen atom or linear alkyl group having 1 to 4 carbon atoms, $R^{07}$ is a hydroxyl group, (meth)acryloyloxy group or group capable of forming a silanol group through hydrolysis, $R^{08}$ is a hydrogen atom, alkyl group having 1 to 6 carbon atoms, hydroxyl group, (meth)acryloyloxy group or group capable of forming a silanol group through hydrolysis, A' is an alkylene group having 2 to 6 carbon atoms, and A" is an alkylene group having 1 to 6 carbon atoms when $R^{08}$ is a hydrogen atom or alkyl group and an alkylene group having 2 to 6 carbon atoms when $R^{08}$ is a hydroxyl group, (meth)acryloyloxy group or group capable of forming a silanol group through hydrolysis.

The group capable of forming a silanol group through hydrolysis represented by $R^{07}$ and $R^{08}$ in the above formula (19) is identical to the group defined for the above silyl monomer.

These amine compounds may be used alone or in combination of two or more. The amount of the amine compound is preferably 0.01 to 20 parts by weight based on 100 parts by weight of the total of all the radically polymerizable monomers when it is used as a catalyst. It is more preferably 0.1 to 10 parts by weight, much more preferably 1 to 10 parts by weight. When the amount is smaller than 0.01 part by weight or larger than 20 parts by weight, it is difficult to obtain the effect of improving adhesion between the coating layer and the substrate. Further when the amount is larger than 20 parts by weight, the coating layer tends to yellow disadvantageously.

100 parts by weight of a polymer compound may be used in place of 100 parts by weight of the above radically polymerizable monomer as the solvent for a molecular compound in the photochromic compound of the present invention. The polymer compound is mixed with the molecular compound as a molten product or a solution thereof.

A known thermoplastic resin may be used as the polymer compound. When the above cured product is used as an optical material, methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane or polycarbonate is preferably used because they have excellent optical properties.

When the polymer compound is used in the form of a solution, a known organic solvent which is known to dissolve a polymer compound can be used according to the type of the polymer compound in use. The concentration of the polymer compound in the polymer compound solution is not particularly limited. For example it may be suitably determined in consideration of moldability and operation efficiency when a film is molded by a casting method or coated.

The photochromic composition of the present invention is obtained by mixing 100 parts by weight of the solvent for a molecular compound comprising the radically polymerizable monomer(s) or the molten polymer(s) or a solution of the polymer compound(s) with 0.01 to 20 parts by weight of "a molecular compound comprising a chromene compound and an aromatic compound". The molecular compound is a compound which is produced by directly bonding the same or different types of stable molecules in a certain ratio, bonding between molecules constituting the molecular compound is gentle and the original structure and bonding property of each constituent molecule rarely change, and which can be dissociated into original constituent molecules relatively easily. In general, the molecular compound is a solid in which constituent molecules are arranged in a certain ratio. When the molecular compound and each constituent molecule are compared with each other, they differ in physical property values such as melting point, boiling point and solubility. When the amount of the molecular compound to be mixed is smaller than 0.01 part by weight, satisfactory photochromism cannot be obtained and when the amount is larger than 20 parts by weight, it is difficult to dissolve the molecular compound uniformly. The amount of the molecular compound is preferably 0.05 to 15 parts by weight, particularly preferably 0.1 to 5 parts by weight based on 100 parts by weight of the solvent for a molecular compound from the viewpoints of photochromism and acquisition ease of a uniform solution.

The above molecular compound used in the present invention is not particularly limited if it is a molecular compound consisting of a chromene compound and an aromatic compound as constituent components and may be a molecular compound consisting of several chromene compounds and several aromatic compounds. The bonding manner of the constituent molecules is not limited and the ratio of the constituent molecules is not limited as well. The ratio is determined for each combination of a chromene compound and an aromatic compound. In the molecular compound which is the photochromic compound of the present invention, the ratio of the number of moles of the chromene compound to the number of moles of the aromatic compound is generally 5:1 to 1:10.

The chromene compound which is one of the constituent components of the molecular compound as the photochromic compound of the present invention is not particularly limited if it can form a molecular compound with an aromatic compound. However, it is preferably a chromene compound having at least one substituted or nonsubstituted phenyl group because it can easily form a molecular compound with an aromatic compound. It is considered that a molecular compound is easily formed by a π electron-π electron interaction between the above substituted phenyl group of the chromene compound and the aromatic compound.

In the present invention, chromene compounds represented by the following formula (1) are particularly preferred out of the chromene compounds having at least one substituted or nonsubstituted phenyl group because they exhibit excellent photochromism:

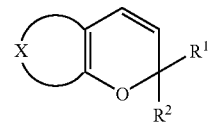

(1)

$R^1$ and $R^2$ in the above formula (1) are each a substituted or nonsubstituted aryl group, or a substituted or nonsubstituted aromatic heterocyclic group, and the divalent group represented by the following formula (2) is a divalent condensed polycyclic organic group which has a benzene ring condensed to a 2H-pyran ring in the above formula (1) and may have a substituent.

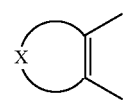

(2)

Examples of the nonsubstituted aryl group and the nonsubstituted aromatic heterocyclic group represented by $R^1$ or $R^2$ include phenyl group, 1- or 2-naphthyl group, 2- or 3-furyl group, 2- or 3-thienyl group and 2- or 3-pyrrolidyl group.

The substituent of the substituted aryl group and the substituted or nonsubstituted aromatic heterocyclic group represented by $R^1$ or $R^2$ are not particularly limited but preferably at least one selected from the group consisting of alkyl group, alkoxy group, aralkoxy group, substituted or nonsubstituted amino group, cyano group, substituted or nonsubstituted aryl group, fluorine atom, chlorine atom, bromine atom, iodine atom, aralkyl group, trifluoromethyl group, trifluoromethoxy group, cyanomethyl group, arylsulfonyl group and alkylsulfonyl group. Examples of the substituent of the above substituted aryl group are the same as those listed for the substituent of the substituted aryl group represented by $R^1$ or $R^2$ excluding the substituted aryl group. Examples of the substituent in the substituted amino group include the above examples of the substituent of the substituted aryl group, substituted or nonsubstituted heterocyclic group having a nitrogen atom as a hetero atom and bonded to a phenyl group by the nitrogen atom, and fused heterocyclic group having an aromatic hydrocarbon ring or aromatic hetero ring condensed to the heterocyclic ring. A hetero atom such as oxygen atom, sulfur atom or nitrogen atom may be existent in the hetero ring besides the nitrogen atom bonded to a phenyl group.

One of $R^1$ and $R^2$ in the above formula (1) is preferably a phenyl group substituted by a substituted or nonsubstituted amino group from the viewpoint of photochromism. Preferred examples of the substituted or nonsubstituted amino group include amino group; alkylamino groups such as methylamino group, ethylamino group, n-propylamino group, i-propylamino group, n-butylamino group and t-butylamino group; dialkylamino groups such as dimethylamino group, diethylamino group, di-n-propylamino group, di-i-propylamino group, di-n-butylamino group and di-t-butylamino group; arylamino groups such as phenylamino group and naphthylamino group; diarylamino groups such as diphenylamino group; and "substituted or nonsubstituted heterocyclic group having a nitrogen atom as a hetero atom and bonded to a phenyl group by the nitrogen atom, or fused heterocyclic group having an aromatic hydrocarbon ring or aromatic hetero ring condensed to the heterocyclic group" having 2 to 10 carbon atoms, particularly 2 to 6 carbon atoms as members of a heterocyclic group, such as morpholino group, piperidino group, pyrrolidinyl group, piperazino group, N-methylpiperazino group and indolinyl group.

The divalent group represented by the above formula (2) in the above formula (1) is a divalent condensed polycyclic organic group which may have a substituent and contains a benzene ring condensed to a 2H-pyran ring in the above formula (1). The group is not particularly limited if a chromene compound bonded to the group exhibits photochromism but preferably a group represented by the following formula (20), (21), (22) or (23) because it exhibits excellent photochromism:

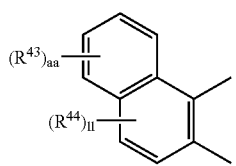
(20)

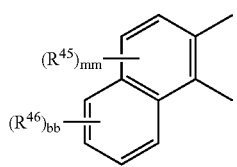
(21)

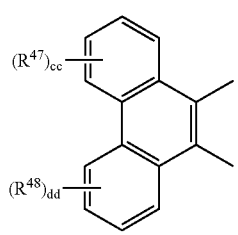
(22)

-continued

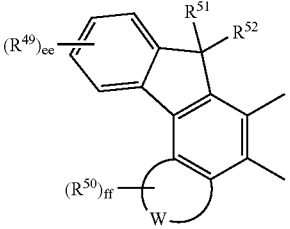
(23)

$R^{43}$ and $R^{44}$ in the above formula (20) are each independently a hydrogen atom, alkyl group, alkoxy group, aralkyloxy group, aralkyl group, carboxy group, alkoxycarbonyl group, aryloxycarbonyl group which may have a substituent, aralkyloxycarbonyl group, amino group which may have a substituent, cyano group, nitro group, aryl group which may have a substituent, halogen atom, heterocyclic group which has a nitrogen atom as a hetero atom and may have a substituent bonded to the ring of a condensed polycyclic organic group by the nitrogen atom, or fused heterocyclic group having an aromatic hydrocarbon ring or aromatic hetero ring bonded to the heterocyclic group. aa indicative of the number of bonded $R^{43}$'s is an integer of 0 to 3, and ll indicative of the number of bonded $R^{44}$'s is an integer of 0 to 2. When aa or ll is 2 or more, bonded $R^{43}$'s or $R^{44}$'s may be the same or different. When $R^{43}$ and $R^{44}$ may have a substituent, the substituent is at least one selected from the group consisting of alkyl group, alkoxy group, aryl group and halogen atom.

In the above formula (21), $R^{45}$ and $R^{46}$ are the same as $R^{43}$ and $R^{44}$ in the above formula (20), respectively, mm indicative of the number of bonded $R^{45}$'s is an integer of 0 to 2, and bb indicative of the number of bonded $R^{46}$'s is an integer of 0 to 3. When mm or bb is 2 or more, bonded $R^{45}$'s or $R^{46}$'s may differ from each other.

In the above formula (22), $R^{47}$ and $R^{48}$ are the same as $R^{43}$ and $R^{44}$ in the above formula (20), respectively, and cc and dd indicative of the number of bonded $R^{47}$'s and $R^{48}$'s are each an integer of 0 to 3. When cc or dd are 2 or more, bonded $R^{47}$'s or $R^{48}$'s may differ from each other.

The group represented by the following formula (24) in the above formula (23) is an aromatic hydrocarbon group or unsaturated heterocyclic group, and $R^{49}$ and $R^{50}$ are the same as $R^{43}$ and $R^{44}$ in the above formula (20), respectively.

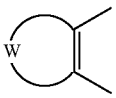
(24)

ee and ff indicative of the number of bonded $R^{49}$'s and $R^{50}$'s are each an integer of 0 to 3. When ee or ff are 2 or more, bonded $R^{49}$'s or $R^{50}$'s may differ from each other. $R^{51}$ and $R^{52}$ are each independently a hydrogen atom, hydroxyl group, alkyl group, alkoxy group, aralkyloxy group, aralkyl group, carboxy group, alkoxycarbonyl group, aryloxycarbonyl group, aralkyloxycarbonyl group, substituted or nonsubstituted amino group, cyano group, nitro group, substituted or nonsubstituted aryl group, or bonded together to form an oxo group, vinylene group which may have a substituent, heterocyclic group which has 1 or 2 oxygen atoms and may have a substituent, aliphatic hydrocarbon ring group which may have a substituent, or a group forming a group represented by the following formula (25):

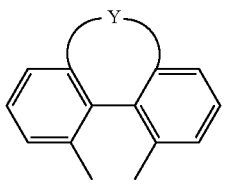
(25)

wherein —Y— is represented by any one of the following formulas:

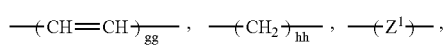

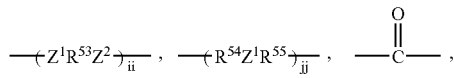

wherein $Z^1$ and $Z^2$ are each independently an oxygen atom or sulfur atom, $R^{53}$, $R^{54}$, $R^{55}$ and $R^{56}$ are each an alkylene group, and gg, hh, ii and jj are each an integer of 1 to 4.

Illustrative examples of the "chromene compound having at least one substituted or nonsubstituted phenyl group" suitable as the chromene compound of the present invention are given below.

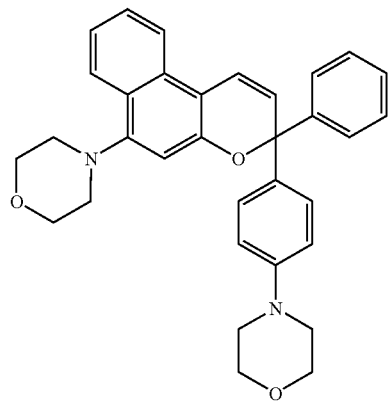

-continued

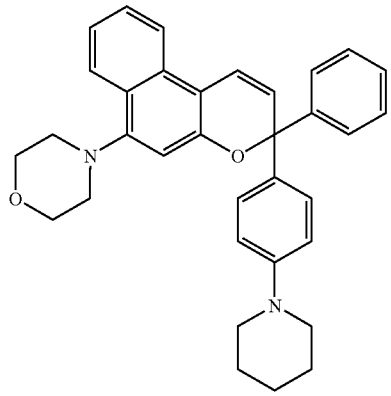

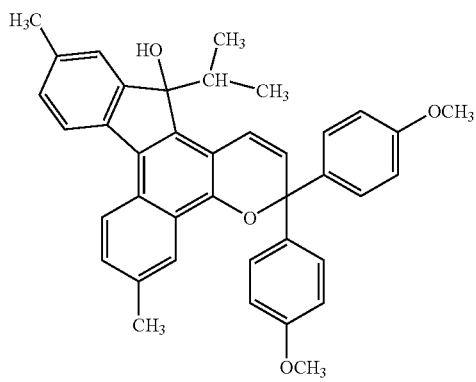

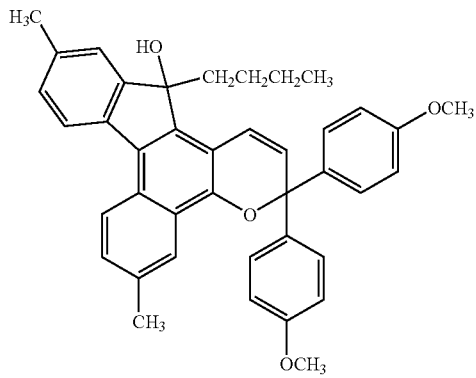

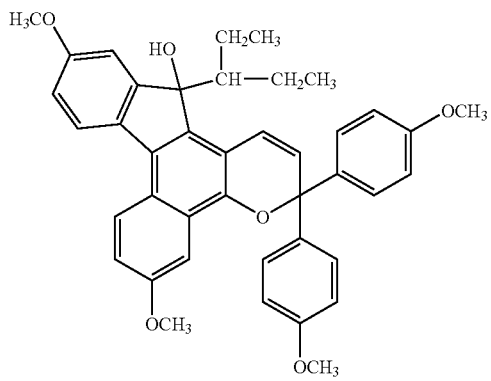

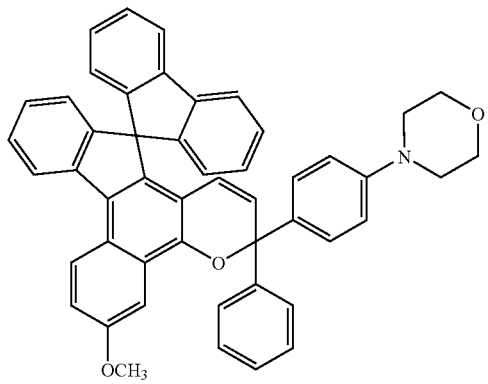
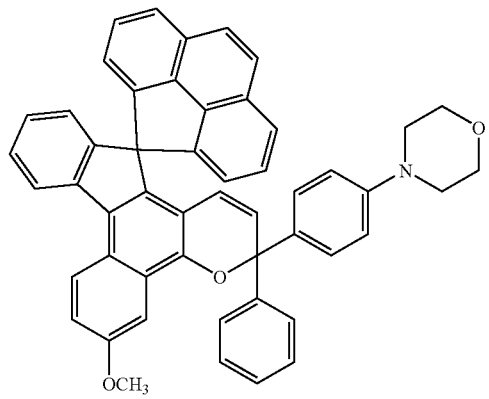
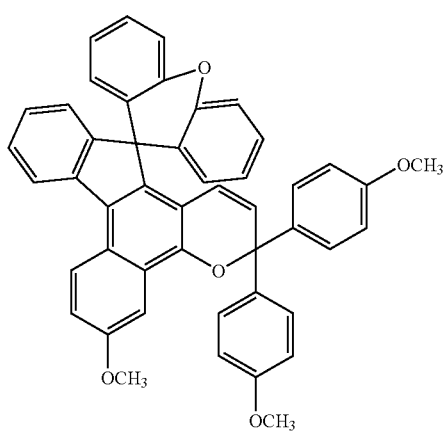
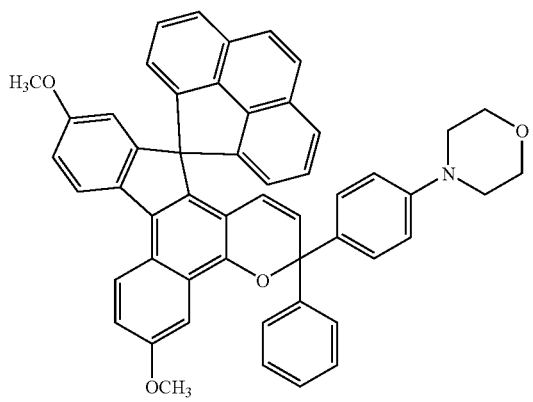
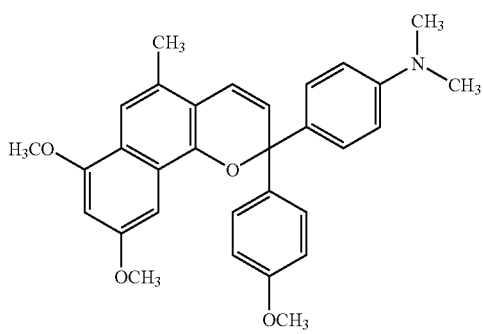
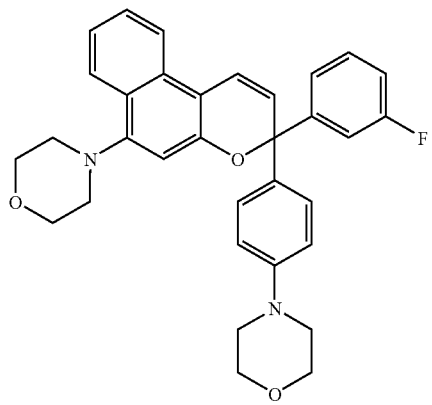
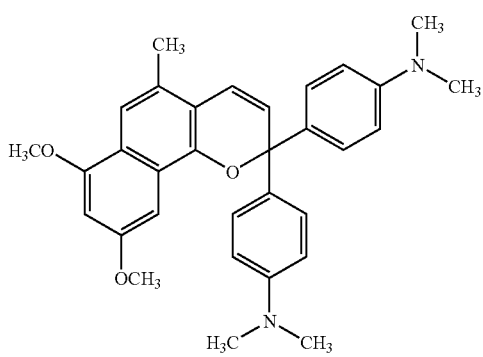
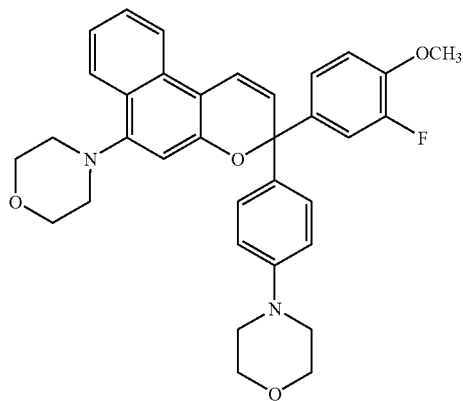

The above chromene compounds are disclosed in the pamphlet of WO98/45281, the pamphlet of WO96/14596, German Laid-open Patent Application DE19902771 A1, the pamphlet of WO98/04937 and the like.

The aromatic compound which is the other constituent molecule of the molecular compound is not particularly limited if it can form the molecular compound with the above chromene compound. However, it is preferably an aromatic compound having a molecular weight of 70 to 150 when the chromene compound has a molecular weight of 300 to 800 because they easily form a molecular compound. It is considered that this is because the aromatic compound can be situated at a position where steric hindrance more hardly occurs and the above π electron-π electron interaction more readily occurs as the molecular weight of the aromatic compound becomes lower. Illustrative examples of the aromatic compound which can be suitably used include toluene, benzene, chlorobenzene, dichlorobenzene, naphthalene, thiophene and pyrrole.

That is, it can be said that a molecular compound of a chromene compound having at least one substituted or nonsubstituted phenyl group, particularly a chromene compound having a molecular weight of 300 to 800 represented by the above formula (1), and an aromatic compound having a molecular weight of 70 to 150 is preferably used as the above molecular compound used as the photochromic material of the present invention from the viewpoints of photochromism and synthesis ease.

The molecular compound of the chromene compound represented by the above formula (1) and the aromatic compound having a molecular weight of 70 to 150 has been unknown and the existence and utility thereof have been discovered by the inventors of the present invention for the first time. The process for producing this molecular compound is not particularly limited. However, the molecular compound can be suitably produced by contacting the aromatic compound having a molecular weight of 70 to 150 to the chromene compound represented by the above formula (1) in a solution to form a molecular compound of the chromene compound and the aromatic compound and precipitating the crystal of the formed molecular compound. As means of contacting the aromatic compound having a molecular weight of 70 to 150 to the chromene compound in the solution, there are (i) a method in which the chromene compound and the aromatic compound are mixed together and heated as required to dissolve the chromene compound in the aromatic compound so as to prepare a uniform solution, and (ii) a method in which the chromene compound and the aromatic compound are mixed with an organic solvent which dissolves both to dissolve the both compounds so as to prepare a uniform solution. In either case, the both compounds are made coexistent in the solution, thereby naturally forming a molecular compound. To take out the formed molecular compound, the solution is concentrated as required and cooled to precipitate the molecular compound as a crystal, or a poor solvent is added to the solution to precipitate the molecular compound as a crystal, and the precipitated crystal is separated by filtration or the like and taken out. A high-purity molecular compound can be obtained by employing these crystallization methods. When the total amount of impurities contained in the solution is small, the solvent is distilled off under conditions which ensure that the molecular compound does not decompose to recover the molecular compound.

In the above methods, the molar ratio of the chromene compound to the aromatic compound to be contacted to each other in the solution is not particularly limited. As a surplus of the aromatic compound can be easily removed, it is preferred to use an excessive amount, particularly 10 to 1,000 moles of the aromatic compound based on 1 mole of the chromene compound from the viewpoint of reaction efficiency. In the above methods, chromene compounds and aromatic compounds may be used alone or in combination.

The molecular compound of the present invention obtained by the above methods is existent as a solid at normal temperature and normal pressure and can be confirmed by the following means (a) to (c).

(a) The melting point of the molecular compound is measured and the measured melting point differs from the phase transition points (melting points or boiling points) of the chromene compound and the aromatic compound forming the molecular compound.

(b) The proton nuclear magnetic resonance spectrum ($^1$H-NMR) of the molecular compound is measured and the proton integral ratios of intrinsic peaks of the chromene compound and the aromatic compound forming the molecular compound are compared with each other to determine the molar ratio of the chromene compound to the aromatic compound.

(c) The ratio of the chromene compound to the aromatic compound can be determined by elemental analysis.

In the photochromic composition of the present invention, another known photochromic compound may be used as a photochromic compound in addition to the above molecular compound in order to adjust the developed color. Any known photochromic compound such as a fulgimide compound, spirooxazine compound or chromene compound may be used as the another photochromic compound. A compound having color development characteristics from which a desired color is obtained is suitably selected as the another photochromic compound according to the type of the molecular compound used. These photochromic compounds may be suitably mixed together to develop a suitable color.

Compounds disclosed in JP-A 2-28154(the term "JP-A" as used herein means an "unexamined published Japanese patent application"), JP-A 62-288830, the pamphlet of WO94/22850, the pamphlet of WO96/14596 and the like can be suitably used as the another photochromic compound.

The compounds newly discovered by the inventors of the present invention as compounds having excellent photochromism, for example, the compounds disclosed in JP-A 2001-114775, 2001-031670, 2001-011067, 2001-011066, 2000-347346, 2000-344762, 2000-344761, 2000-327676, 2000-327675, 2000-256347, 2000-229976, 2000-229975, 2000-229974, 2000-229973, 2000-229972, 2000-219687, 2000-219686, 2000-219685, 11-322739, 11-286484, 11-279171, 10-298176, 09-218301, 09-124645, 08-295690, 08-176139 and 08-157467 may be suitably used as well.

Out of these photochromic compounds, chromene-based photochromic compounds are particularly preferred because they have higher photochromism durability than other photochromic compounds and much higher color development intensity and fading speed than other photochromic compounds. When a chromene compound is used as the another photochromic compound, it should be used in a state that it does not form a molecular compound with an aromatic compound. Therefore, a chromene compound which is not used in the form of a molecular compound is included in the another photochromic compound even though it is a chromene compound represented by the above formula (1).

Examples of the chromene compound suitably used as the another photochromic compound are chromene compounds having the following structures.

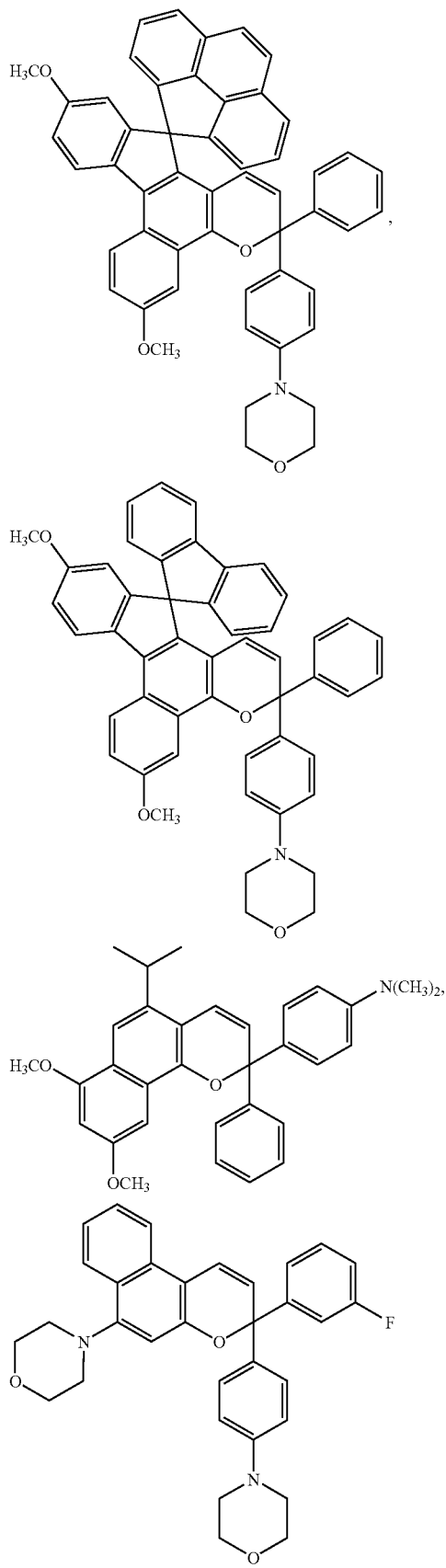

In the photochromic composition of the present invention, the amount of the another photochromic compound which may be added besides the above molecular compound may be suitably determined according to a desired color and not particularly limited but preferably 0.01 to 10 parts by weight, particularly preferably 0.01 to 5 parts by weight based on 100 parts by weight of the solvent for a molecular compound. When the amount of the another photochromic compound is smaller than 0.01 part by weight, the color development intensity becomes low and a satisfactory color control function is not obtained and when the amount is larger than 10 parts by weight, it is difficult to dissolve it in the solvent uniformly with the result that color development nonuniformity may occur.

Out of the photochromic compositions of the present invention, a photochromic composition which comprises a radically polymerizable composition as the solvent for a molecular compound can be suitably used as a coating for optical materials. In this case, even when the obtained coating layer is thin, sufficiently high color development intensity can be obtained by increasing the concentration of the photochromic compound. When the coating layer is thick, appropriate color development intensity can be obtained by reducing the amount of the molecular compound used (that is, the amount of the chromene compound). For instance, when the photochromic composition is used as a coating for spectacle lenses and the thickness of the coating layer is about 10 μm, the photochromic compound is used in an amount of 5 to 0.15 parts by weight based on 100 parts by weight of the total of all the radically polymerizable monomers and when the thickness of the coating layer is about 50 μm, the photochromic compound is used in an amount of 0.1 to 1 part by weight to obtain preferred color development intensity.

To the photochromic composition or coating composition of the present invention may be added additives such as a surfactant, antioxidant, radical scavenger, ultraviolet light stabilizer, ultraviolet light absorber, release agent, discoloration preventing agent, antistatic agent, fluorescent dye, dye, pigment, perfume and plasticizer to improve the durability, color development speed, fading speed and moldability of the photochromic compound. When the solvent for a molecular compound is a radically polymerizable monomer, it is extremely preferred to add a polymerization initiator which will be described hereinafter to cure the composition. Any known compounds may be used as the above additives.

For example, the surfactant may be nonionic, anionic or cationic and a nonionic surfactant is preferred from the viewpoint of solubility in polymerizable monomers. Preferred examples of the nonionic surfactant include sorbitan fatty acid ester, glycerin fatty acid ester, decaglycerin fatty acid ester, propylene glycol-pentaerythritol fatty acid ester, polyoxyethylene sorbitan fatty acid ester, polyoxyethylene sorbitol fatty acid ester, polyoxyethylene glycerin fatty acid ester, polyethylene glycol fatty acid ester, polyoxyethylene alkyl ether, polyoxyethylene phytosterol-phytostanol, polyoxyethylene polyoxypropylene alkyl ether, polyoxyethylene alkyl phenyl ether, polyoxyethylene castor oil-cured castor oil, polyoxyethylene lanolin-lanolin alcohol-bees wax derivative, polyoxyethylene alkylamine-fatty acid amide, polyoxyethylene alkyl phenyl formaldehyde condensate and single chain polyoxyethylene alkyl ether. The above surfactants may be used in combination of two or more. The amount of the surfactant is preferably 0.1 to 20 parts by weight based on 100 parts by weight of the solvent for a molecular compound.

As the antioxidant, radical scavenger, ultraviolet light stabilizer and ultraviolet light absorber may be preferably used a hindered amine optical stabilizer, hindered phenol antioxidant, phenol-based radical scavenger, sulfur-based antioxidant, benzotriazole-based compound, benzophenone-based compound and the like. These antioxidants, radical scavengers, ultraviolet light stabilizers and ultraviolet light absorbers may be used in combination of two or more. As for use of these nonpolymerizable compounds, a surfactant and an antioxidant, radical scavenger, ultraviolet light stabilizer or ultraviolet light absorber may be used in combination. The amount of the antioxidant, radical scavenger, ultraviolet light stabilizer or ultraviolet light absorber is preferably 0.001 to 20 parts by weight based on 100 parts by weigh of the solvent for a molecular compound.

Out of the above stabilizers, a hindered amine optical stabilizer is particularly preferably used to prevent the deterioration of the photochromic compound when the composition of the present invention is used as a coating and cured, or to improve the durability of a cured product thereof. The above hindered amine compounds afore-mentioned as the amine compound having no catalytic function are used as the hindered amine optical stabilizer. Out of these, bis(1,2,2,6,6-pentamethyl-4-piperidyl)sebacate and Adecastab LA-52, LA-62, LA-77 and LA-82 of Asahi Denka Kogyo K.K. are particularly preferred because they have a great effect of preventing the deterioration of the photochromic compound. The amount of the hindered amine is preferably 0.001 to 20 parts by weight, particularly preferably 0.1 to 10 parts by weight, the most preferably 1 to 10 parts by weight based on 100 parts by weight of the total of all the radically polymerizable monomers.

The process for preparing the photochromic composition of the present invention is not particularly limited. Predetermined amounts of components are weighed and mixed together to obtain the photochromic composition of the present invention. The order of adding the components is not particularly limited. For instance, to prepare the above composition suitable for use as a coating, all the components may be added at the same time, or only monomer components are mixed together and a photochromic compound, other additives and further a photopolymerization initiator may be added to and mixed with the above mixture right before polymerization as will be described hereinafter.

When the photochromic composition of the present invention is obtained by mixing together the radically polymerizable monomers and the above molecular compound, the viscosity at 25° C. thereof is preferably 20 to 500 cp. When it is used as a coating for an optical article such as a spectacle lens, the viscosity at 25° C. thereof is preferably 50 to 300 cp, particularly preferably 60 to 200 cp. Within the above viscosity range, the thickness of the coating layer can be easily adjusted to a range from 10 to 100 μm and photochromism can be developed to the full.

When the solvent of the photochromic composition of the present invention is a radically polymerizable monomer and the radically polymerizable monomer includes both an epoxy-based monomer and an amine compound, the epoxy-based monomer and the amine compound are preferably packed separately and mixed together before use from the viewpoint of keeping stability. In this case, other components may be suitably divided and contained in the above two packages.

The method of curing the photochromic compound of the present invention differs according to the type of the solvent for a molecular compound of the composition. When the solvent for a molecular compound is a radically polymerizable monomer, a polymerization initiator is added to cure the radically polymerizable monomer by polymerization. When the solvent for a molecular compound is a polymer compound in a molten state, the photochromic compound is cured by cooling. When the solvent for a molecular compound is a solution of a polymer compound, the solvent of the solution is removed by vaporization.

The method of curing the photochromic compound of the present invention by polymerization when the solvent for a molecular compound is a radically polymerizable monomer is not particularly limited and a known polymerization method may be employed according to the type of the radically polymerizable monomer used. Polymerization initiating means is use of a radical polymerization initiator such as a peroxide or azo compound, exposure to radiation such as ultraviolet radiation, α-ray, β-ray or γ-ray, or both of them.

The radical polymerization initiator is not particularly limited and any known radical polymerization initiator may be used. Typical examples of the thermopolymerization initiator include diacyl peroxides such as benzoyl peroxide, p-chlorobenzoyl peroxide, decanoyl peroxide, lauroyl peroxide and acetyl peroxide; peroxy esters such as t-butylperoxy-2-ethyl hexanoate, t-butylperoxy dicarbonate, cumylperoxy neodecanate and t-butylperoxy benzoate; percarbonates such as diisopropylperoxy dicarbonate, di-2-ethylhexylperoxy dicarbonate and di-sec-butyloxy carbonate; and azo compounds such as 2,2'-azobisisobutyronitrile, 2,2'-azobis(4-dimethylvaleronitrile), 2,2'-azobis(2-methylbutyronitrile) and 1,1'-azobis(cyclohexane-1-carbonitrile).

The amount of the thermopolymerization initiator differs according to polymerization conditions, the type of the initiator and the types and ratio of the polymerizable monomers and cannot be limited unconditionally. In general, it is preferably 0.01 to 10 parts by weight based on 100 parts by weight of the total of all the radically polymerizable monomers. The above thermopolymerization initiators may be used alone or in combination of two or more.

For polymerization by exposure to light such as ultraviolet radiation, it is preferred to use a photopolymerization initiator such as benzoin, benzoin methyl ether, benzoin butyl ether, benzophenol, acetophenone, 4,4'-dichlorobenzophenone, diethoxyacetophenone, 2-hydroxy-2-methyl-1-phenylpropan-1-one, benzyl methyl ketal, 1-(4-isopropylphenyl)-2-hydroxy-2-methylpropan-1-one, 1-hydroxycyclohexylphenyl ketone, 2-isopropylthioxanthone, bis(2,6-dimethoxybenzoyl-2,4,4-trimethyl-pentylphosphine oxide, bis(2,4,6-trimethylbenzoyl)-phenylphosphine oxide, 2,4,6-trimethylbenzoyldiphenylphosphine oxide or 2-benzyl-2-dimethylamino-1-(4-morpholinophenyl)-butanone-1.

The above photopolymerization initiators may be used alone or in combination of two or more. The above thermopolymerization initiators and the above photopolymerization initiators may be used in combination.

The photopolymerization initiator is used in an amount of preferably 0.001 to 10 parts by weight, more preferably 0.001 to 5 parts by weight based on 100 parts by weight of the total of all the monomers.

The particularly preferred polymerization method is that the curable composition of the present invention which comprises the above photopolymerization initiator is exposed to ultraviolet radiation to be cured and further heated to complete polymerization.

When polymerization is carried out by exposure to ultraviolet radiation or the like, any known light source may be used. Examples of the light source include super high-pressure mercury lamp, high-pressure mercury lamp, low-pressure mercury lamp, xenon lamp, carbon arc, bactericidal lamp, metal halide lamp and electrodeless lamp. The exposure time when the above light source is used may be suitably determined according to the type, absorption wavelength and sensitivity of the above photopolymerization initiator, the thickness of the photochromic layer and the like. When an electron beam is used as a light source, the photochromic layer can be cured without adding a photopolymerization initiator.

Although the photochromic composition of the present invention can be used alone as a photochromic material when it is cured, as the photochromic compound is dispersed uniformly in a high concentration, it can be particularly suitably used as a film forming composition or a coating for a substrate, for example, an optical material such as a spectacle lens, making use of the fact that a cured product having high color development intensity can be obtained though the thickness thereof is small.

When the photochromic composition of the present invention is used as a coating, the optical material as a substrate therefor is not particularly limited and may be a known optical material such as a spectacle lens or window glass for houses and automobiles.

Examples of the known spectacle lens include plastic-based spectacle lenses such as (meth)acrylic resin, polycarbonate-based resin, allyl-based resin, thiourethane-based resin, urethane-based resin and thioepoxy-based resin spectacle lenses, and glass-based spectacle lenses. The photochromic composition (as a coating) of the present invention may be used for all of the above spectacle lenses but it is preferably used for plastic-based spectacle lenses because it has excellent adhesion to plastics. It is particularly preferably used as a coating composition for (meth)acrylic resin, polycarbonate-based resin, allyl-based resin, thiourethane-based resin, urethane-based resin and thioepoxy-based resin spectacle lenses.

When the composition of the present invention is used as a coating composition for an optical material such as a spectacle lens, it is preferred that the composition of the present invention (coating of the present invention) be applied to the optical material by spin coating, spray coating, dip coating, dip-spin coating or the like and cured by exposure to light or heating. More preferably, it is cured by exposure to light and then heating to complete polymerization.

When the coating composition of the present invention is to be applied to at least one side of the above substrate and cured, as described above, it can be cured optically or/and thermally by using an optically or/and thermally radical polymerization initiator(s). From the viewpoint of the uniformity of the obtained film, curing is preferably carried out under the condition that molecular oxygen is substantially nonexistent (the expression "substantially nonexistent" means that the concentration of the molecular oxygen is 10,000 ppm or less, preferably 1,000 ppm or less). As for the curing method, the coating composition of the present invention is injected into a space formed by the substrate and a glass mold through a resin support material to be cured, or the coating composition is polymerized after the curing atmosphere is substituted by an inert gas. Any inert gas may be used if it is inactive with the radical containing no oxygen. Inexpensive nitrogen or argon gas having a high substituting effect may be used. Although the concentration of oxygen is preferably as low as possible because polymerization is hardly prevented, as oxygen cannot be completely eliminated when the atmosphere is substituted, a trace amount of molecular oxygen is inevitably contained. Therefore, the concentration of oxygen in the gas is preferably 10,000 ppm or less, more preferably 1,000 ppm or less because the above ill effect can be eliminated.

To coat the substrate such as a spectacle lens with the coating composition of the present invention, before application of the coating composition, the substrate is preferably subjected to an atmospheric-pressure plasma treatment. In general, the term "atmospheric-pressure plasma treatment" means a treatment at a higher pressure than a low-pressure plasma treatment. The pressure of the treatment is higher than about 1 torr which is the pressure of a low-pressure plasma treatment. When a plasma treatment is carried out at the atmospheric pressure, the surface of a resin substrate can be treated more uniformly than when the treatment is carried out at a pressure other than the atmospheric pressure, for example, a vacuum plasma treatment and the structure of an apparatus can be simplified because it does not require severe air tightness.

A known gas is used as an introduction gas used for the atmospheric-pressure plasma treatment. Examples of the introduction gas is air, nitrogen, oxygen, hydrogen, carbon dioxide, carbon monoxide, sulfur dioxide, argon, helium, neon, ammonia, chlorine, nitrogen monoxide, nitrogen dioxide and Freon-based gas such as $CF_4$ or $C_2F_6$. Air or nitrogen is preferably used from the viewpoints of handling ease and cost.

The introduction gas used for the atmospheric-pressure plasma treatment which depends on other conditions preferably has a relative humidity of 80% RH or less, more preferably 40% RH or less at 24° C. The temperature for limiting the relative humidity is 24° C. but the temperature of the introduction gas used for the atmospheric-pressure plasma is not limited. The above relative humidity of the introduction gas is a value before it is introduced into an atmospheric-pressure plasma exposure unit. By setting the relative humidity to the above value, the effect of improving adhesion by the atmospheric-pressure plasma treatment becomes extremely large.

The method of producing the introduction gas having the above relative humidity is not particularly limited. When a gas other than air in environment is used, a gas taken out from a commercially available gas cylinder generally has a relative humidity lower than the above value. When air in environment is used, untreated air at a site where the atmospheric-pressure plasma exposure unit is installed or air obtained by passing the untreated air through a water absorption pipe filled with a suitable amount of a moisture absorbent such as calcium chloride or silica gel to adjust its relative humidity after it is compressed by a compressor is used. As a matter of course, if the relative humidity of air in environment is sufficiently low, it does not need to be let pass through the water absorption pipe.

The temperature of the introduction gas used for the atmospheric-pressure plasma treatment is not particularly limited but preferably −5 to 100° C., more preferably 5 to 60° C.

The method of exposing plasma in the atmospheric-pressure plasma treatment is not particularly limited but the following methods are preferably used.

That is, (1) the resin substrate is placed on a spin coater and exposed to plasma while it is turned, (2) the resin substrate is placed below a fixed plasma exposure site and moved in longitudinal and transverse directions automatically or manually so that the surface of the resin substrate is uniformly treated with plasma, or (3) the resin substrate is fixed and the plasma exposure site is moved in longitudinal and transverse directions automatically or manually so that the surface of the resin substrate is uniformly treated with plasma.

In the atmospheric-pressure plasma treatment, a mesh-like sheet made from metal (including alloy) such as iron, copper, aluminum, stainless steel or SUS may be inserted between the resin substrate and the plasma exposure site. By using the mesh-like sheet, the deterioration by discharge or heat of the surface of the resin substrate used for the atmospheric-pressure plasma treatment can be reduced and the atmospheric-pressure plasma treatment can be carried out efficiently without deteriorating the surface of the resin substrate. Further, when the mesh-like sheet is used, relatively high adhesion can be obtained without carrying out the step of cleaning with water or an organic solvent after the atmospheric-pressure plasma treatment which will be described hereinafter.

The surface of the resin substrate may be coated with a coating composition comprising a molecular compound after it is subjected to the above atmospheric-pressure plasma treatment. Preferably, the surface subjected to the above atmospheric-pressure plasma treatment is cleaned with a solvent (to be referred to as "cleaning solvent" hereinafter) before coating. This cleaning makes it easier to ensure adhesion between the surface of the resin substrate and a cured product. Cleaning with this cleaning solvent is particularly effective when the above metal mesh-like sheet is not used for the atmospheric-pressure plasma treatment.

Examples of the cleaning solvent include water; alcohols such as methanol, ethanol and isopropanol; ethers such as tetrahydrofurane and dioxane; organic solvents which are miscible with water in any ratio at normal temperature, such as acetonitrile and acetone; and other organic solvents such as 1-butyl alcohol, 2-butyl alcohol, methyl acetate, ethyl acetate, diethyl ether, hexane and toluene.

These cleaning solvents may be used alone or as a mixture. It is extremely preferred from the viewpoint of an adhesion improving effect that water be contained as one component. It is the most preferred to use water because the adhesion improving effect is obtained with extremely high reproducibility and the disposal of waste water is extremely easy.

When a mixed solvent of water and an organic solvent is used, it is particularly preferred that the organic solvent be uniformly mixed with water. To prepare this uniform mixed solvent of water and an organic solvent, a water-soluble organic solvent which is miscible with water in any ratio at normal temperature is preferably used as the organic solvent. The water-soluble organic solvent is preferably methanol, ethanol or acetone because they are easily handled and harmless to the human body.

When the cleaning solvent is a water or a uniform mixed solvent of water and an organic solvent, the mass ratio of water to the organic solvent is preferably in the range of 100/0 to 1/99, more preferably 100/0 to 15/85.

Commercially available solvents for industrial application can be used without purification as the cleaning organic solvent, and city water, ion exchange water, distilled water, pure water and the like may be used as water.

The temperature of the cleaning solvent, which differs according to the type of the resin substrate used and the types and mixing ratio of water and the organic solvent used for cleaning, is preferably −5 to 100° C., more preferably 5 to 80° C.

Any known method may be used to clean the surface of the resin substrate with the cleaning solvent after the atmospheric-pressure plasma treatment. Preferred methods include (1) one in which the surface is cleaned with a cloth impregnated with the cleaning solvent, (2) supersonic cleaning, and (3) one in which the surface is cleaned with a spin coater. More specifically, in the method (1), a cloth is impregnated with a suitable amount of the cleaning solvent and used to wipe the surface of the resin substrate subjected to the atmospheric-pressure plasma treatment therewith. In the method (2), the cleaning solvent is poured into a vessel and the resin substrate subjected to the atmospheric-pressure plasma treatment is immersed in the cleaning solvent to be cleaned ultrasonically. In the method (3), the resin substrate subjected to the atmospheric-pressure plasma treatment is placed on a spin coater, a suitable amount of the cleaning solvent is applied (dropped) to the surface of the resin substrate, and then the resin substrate is cleaned while it is turned.

The number of times of carrying out the above cleaning method is not particularly limited but preferably 0 to 10, more preferably 1 to 5 from the viewpoint of productivity. Two or more of the cleaning methods (1) to (3) may be carried out on one resin substrate subjected to the atmospheric-pressure plasma treatment. When the substrate is to be cleaned a plurality of times, a different cleaning solvent may be used each time it is cleaned.

The cleaning time, which differs according to the types, amounts and temperatures of the used resin substrate and the cleaning solvent and further the cleaning method, is preferably 1 second to 30 minutes, more preferably 3 seconds to 10 minutes.

In the above methods, sufficient adhesion is obtained by applying a curable coating composition comprising a photochromic compound to the surface of the resin substrate subjected to the atmospheric-pressure plasma treatment after it is cleaned with a cleaning solvent as required and curing the curable coating composition. Since adhesion is further improved by treating the resin substrate with an alkali solution before or after the plasma treatment of the resin substrate, the above method can be preferably used. The alkali solution is preferably an aqueous solution of sodium hydroxide or an aqueous solution of potassium hydroxide. The concentration of the hydroxide is preferably 5 to 30 parts by mass. The temperature is not particularly limited and may be suitably determined in consideration of the heat resistance of the substrate in use. It is preferably in the range of 20 to 60° C. As for the treatment method, the resin substrate is impregnated with the alkali solution or ultrasonically cleaned while it is impregnated. The treatment time, which differs according to treating conditions, is preferably 1 minute to 1 hour, more preferably 5 to 15 minutes. The alkali solution may be a mixed solution of water and an alcohol solvent or an alcohol solution, besides an aqueous solution. The alcohol to be used is a lower alcohol such as methanol, ethanol or isopropyl alcohol. An organic base such as 1-methyl-2-pyrrolidone may be further added as an additive in an amount of 1 to 10 parts by mass based on 100 parts by mass of the alkali solution.

The thickness of the coating layer obtained by curing in accordance with the above method is not particularly limited but preferably relatively large because sufficient color development intensity is obtained and the durability of photochromism is satisfactory even though the concentration of the photochromic compound is low. However, as the thickness of the coating layer becomes larger, initial yellowness increases. Therefore, the thickness of the coating layer is preferably 10 to 100 µm, more preferably 20 to 50 µm. This coating thickness can be easily obtained by adjusting the viscosity at 25° C. of the curable composition to preferably 20 to 500 cp, more preferably 50 to 300 cp, much more preferably 60 to 200 cp. Conventionally known coating compositions (which do not contain a silyl monomer, photochromic material, etc.) contain a solvent to obtain a uniform film and accordingly has a viscosity of 5 cp or less, and the thickness of a coating layer obtained therefrom is several µm or less.

When the composition of the present invention is used as a coating composition for a spectacle lens, the ratio of components of the composition, particularly the radically polymerizable monomer is preferably adjusted to ensure that the refractive index of a cured product thereof becomes almost equal to that of the spectacle lens. Generally speaking, the refractive index is adjusted to about 1.48 to 1.75.

When the composition of the present invention comprises the above silyl monomer and/or isocyanate monomer and the amine compound and is used as a coating composition for an optical material such as a spectacle lens, particularly a plastic-based spectacle lens, it exhibits extremely high adhesion to the optical material.

Although the thus coated optical material can be directly used as a photochromic optical material, it is more preferably coated with a hard coat material. When it is coated with a hard coat material, the scratching resistance of the photochromic optical material can be improved.

Any known hard coat material can be used, as exemplified by silan coupling agents, hard coatings essentially composed of a sol of an oxide of silicon, zirconium, antimony or aluminum, and hard coatings essentially composed of an organic polymer. The curable composition of the present invention has high adhesion to a hard coat which conventionally known compositions have poor adhesion to and are therefore difficult to be used with and which is cured by a condensation method and is therefore extremely useful. Further, processing and a secondary treatment such as antireflection treatment and antistatic treatment may be made on the surface of a single cured product of the curable composition of the present invention, the cured surface of a coating material for an optical material or the hard coated surface of the coating layer by depositing a thin film of a metal oxide such as $SiO_2$, $TiO_2$ or $ZrO_2$ or applying an organic polymer to form a thin film.

Since the molecular compound of the present invention shows the same excellent photochromism as the chromene compound constituting the molecular compound, it can be used as a recording material such as a recording material substituting a silver salt photosensitive material, copy material, printing photosensitive material, recording material for cathode ray tubes, laser photosensitive material or holography photosensitive material.

The molecular compound of the present invention is soluble in general organic solvents such as toluene, chloroform and tetrahydrofuran, monomers and molten polymers and is quickly dissolved. For instance, the dissolution time of the molecular compound when it is dissolved in a high concentration is much shorter than the dissolution time of only a chromene compound which is not in the form of a molecular compound. A solution or dispersion in a polymer solid matrix of the molecular compound shows an excellent reversible photochromic function that it is almost achromatic and transparent when it is not exposed to light, develops a color quickly upon exposure to sunlight or ultraviolet radiation and returns to its original breached state quickly when light is shut off. Since a photochromic compound can be uniformly dispersed in a polymer matrix in a high concentration by dissolving the molecular compound of the present invention in a monomer or a molten polymer to prepare the photochromic composition of the present invention and curing the composition, even when the thickness of the polymer matrix layer is small, high color development intensity can be obtained. Therefore, various methods of providing photochromism to materials can be employed. For instance, in addition to the above coating, a method in which a polymer film comprising a photochromic compound uniformly dispersed in a high concentration is obtained by using the molecular compound of the present invention and sandwiched between lenses; a method in which the surface of a lens is covered with the polymer film and further with a curable substance; a method in which the molecular compound of the present invention is dissolved in silicone oil, the resulting solution is impregnated into the surface of a lens by heating at 150 to 200° C. for 10 to 60 minutes and the surface of the lens is coated with a curable substance are employed to obtain a photochromic lens having uniform light control performance.

EXAMPLES

The following examples are provided for the purpose of further illustrating the present invention but are in no way to be taken as limiting.

Production Example 1

10 g (21.6 mmol) of the following hydroxyl compound and 10.1 g (35 mmol) of the following propargyl alcohol derivative were dissolved in 500 ml of toluene, and further 0.5 g of p-toluenesulfonic acid was added to reflux the resulting solution for 1 hour. Thereafter, the obtained chromene compound (C) shown below was purified by silica gel column chromatography to produce 7.2 g of a product having an HPLC purity of 99% (yield of 45%).

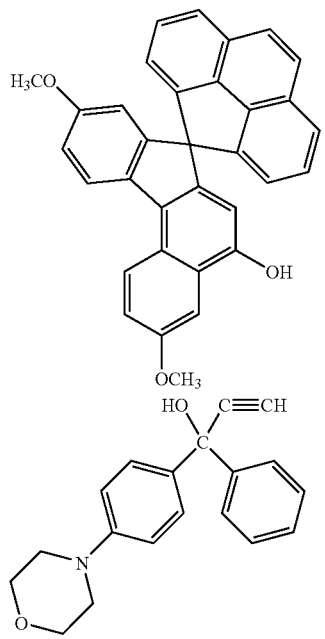

(C)

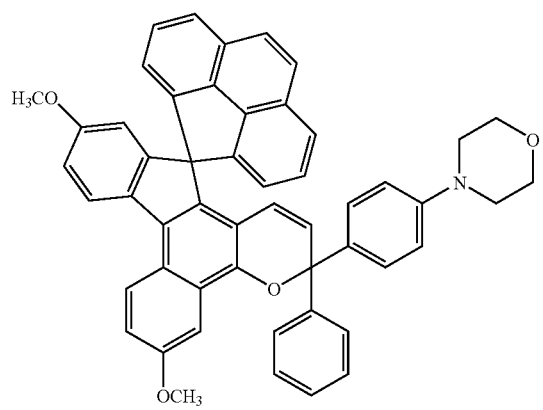

Production Example 2

10 g (43 mmol) of the following naphthalene derivative and 15 g (47 mmol) of the following propargyl alcohol derivative were dissolved in 500 ml of toluene, and further 0.5 g of p-toluenesulfonic acid was added to reflux the resulting solution for 1 hour. Thereafter, the obtained chromene compound (D) shown below was purified by silica gel column chromatography to produce 5.6 g of a product having an HPLC purity of 99% (yield of 25%).

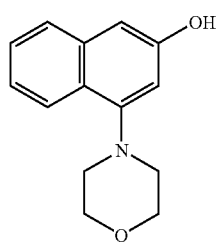

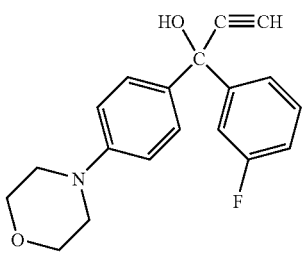

(D)

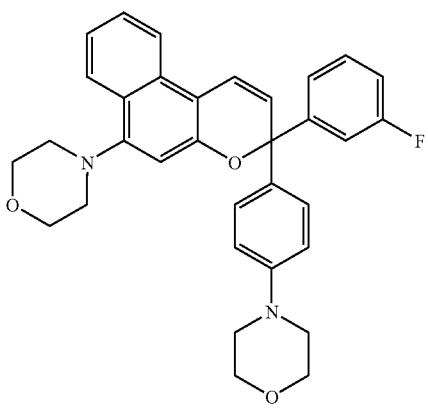

Example 1

10 g (21.6 mmol) of the following hydroxyl compound and 10.1 g (35 mmol) of the following propargyl alcohol derivative were dissolved in 500 ml of toluene, and further 0.5 g of p-toluenesulfonic acid was added to reflux the resulting solution for 1 hour.

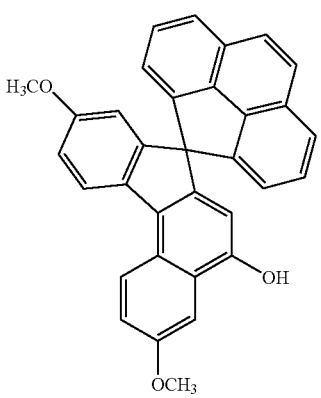

-continued

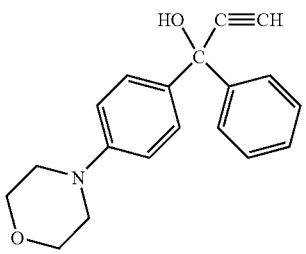

The toluene solution obtained after the reaction mixture was washed with water to remove p-toluenesulfonic acid solvent was concentrated by distilling off toluene under reduced pressure. When the solution was concentrated until the amount of the remaining solution of the reaction mixture became about 100 ml and stirred at room temperature for 24 hours, an ocher crystal was precipitated. When the obtained crystal was filtered, 8 g of an ocher powdery crystal was obtained. The crystal was dissolved in 80 ml of toluene (10 times the volume of the obtained crystal) by heating and stirred at room temperature for 24 hours to be recrystallized and filtered. The same operation was repeated 5 times to produce about 1 g of a yellow powdery crystal. When the collected product was dried at 80° C. under reduced pressure until a weight reduction was not seen, 0.5 g of a yellow powdery crystal was obtained.

When elemental analysis was made on the crystal, the crystal contained 85.01% of C, 5.70% of H, 1.59% of N and 7.74% of O which did not agree with the calculated values of the chromene compound (C) alone but agreed very closely with the calculated values of a molecular compound of the chromene compound (C) and toluene in a ratio of 1:1 (84.97% of C, 5.68% of H, 1.68% of N and 7.67% of O). When the proton nuclear magnetic resonance spectrum of the crystal was measured, peaks derived from the chromene compound (C), that is, a peak corresponding to 25H at δ of 5.0 to 8.6 ppm based on an aromatic proton and alkene proton, a peak corresponding to 6H at δ of 4.0 ppm and 3.5 ppm based on a methoxy group, a peak corresponding to 4H at δ of 3.8 ppm and 3.1 ppm based on a morpholino group; and a peak corresponding to 3H at δ of 2.36 ppm based on a methyl group of toluene, and a peak corresponding to 5H at δ of 7.2 to 7.3 ppm based on the aromatic proton of toluene were confirmed. It was found from comparison of integral values that the molar ratio of the chromene compound (C) to toluene was 1:1. The NMR chart of the molecular compound is shown in FIG. 1. Further, when the melting point of the above crystal was measured with the EX-PAR6000 differential thermal analyzer of Seiko Instruments Inc., no heat absorption peak was observed except 162° C. which was the melting point of the crystal and no heat absorption peak was observed even at 110° C. which was the boiling point of toluene. The chart of differential thermal analysis is shown in FIG. 2. It was confirmed from the above results that toluene as a solvent did not simply adhere to the chromene compound (C) in the above crystal but the above crystal was the molecular compound of the chromene compound and toluene.

In order to investigate the dissolution speed of the above molecular compound in a monomer, 5 parts by weight of the molecular compound was added to a monomer solution which was a mixture of 70 parts by weight of tetraethylene glycol dimethacrylate, 15 parts by weight of triethylene glycol dimethacrylate, 10 parts by weight of glycidyl methacrylate and 5 parts by weight of 2-hydroethyl methacrylate at 25° C. and fully stirred to measure the time elapsed until it was completely dissolved by the eye. Although the amount of the molecular compound was large at 5 parts by weight, the time required for complete dissolution was only 6 minutes, which means that it dissolved quickly.

Example 2

1 g of the chromene compound (D) after purification obtained in Production Example 2 was added to 5 ml of toluene, dissolved by heating, naturally cooled to room temperature, and stirred overnight at room temperature to precipitate a crystal. The precipitated crystal powder was collected by filtration and the collected product was dried at 80° C. under reduced pressure until a weight reduction was not seen to produce 0.46 g of a yellow powdery crystal.

When elemental analytical was made on the crystal, the crystal contained 78.20% of C, 6.45% of H, 3.11% of F, 4.66% of N and 7.88% of O which did not agree with the calculated value of the chromene compound (D) alone but agreed very closely with the calculated values of a 1:1 molecular compound of the chromene compound (D) and toluene (78.15% of C, 6.39% of H, 4.56% of N and 7.81% of O). When the proton nuclear magnetic resonance spectrum of the crystal was measured, peaks derived from the chromene compound (D), that is, a peak corresponding to 16H at δ of 3.0 to 3.1 ppm and 3.7 to 3.8 ppm based on a morpholino group and a peak corresponding to 15H at δ of 6.0 to 8.4 ppm based on an aromatic proton and alkene proton; and a peak corresponding to 3H at δ of 2.36 ppm based on the methyl group of toluene and a peak corresponding to 5H at δ of 7.2 to 7.3 ppm based on the aromatic proton of toluene were confirmed. It was found by comparison of integrated values that the molar ratio of the chromene compound (D) to toluene was 1:1. The melting point and the dissolution speed were measured in the same manner was in Example 1. The melting point and the dissolution speed are shown in Table 1.

TABLE 1

| | Constituent molecules of molecular compound | | properties of molecular compound | |
|---|---|---|---|---|
| No. | Chromene compound | aromatic compound (molecular weight) | melting point (° C.) | amount/dissolution speed (parts by weight)/(hour) |
| Ex.1 | [structure: chromene compound with H₃CO, OCH₃, morpholino-phenyl, and phenyl substituents on a spiro-fluorene/acenaphthylene system] | Toluene (92) | 162 | 5/0.1 |
| Ex.2 | [structure: naphthopyran with morpholino substituent, 3-fluorophenyl and 4-morpholinophenyl groups] | Toluene (92) | 113 | 5/0.05 |

Ex.: Example

Comparative Example 1

1 g of the purified chromene compound (C) obtained in Production Example 1 was dissolved in 20 ml of ethyl acetate by heating and stirred overnight at room temperature. The precipitated powder was filtered and dried at 80° C. under reduced pressure until a weight reduction was not seen to produce 0.77 g of a light green crystal. The elemental analysis values of the crystal were 84.20% of C, 5.33% of H, 1.99% of N and 8.68% of O which agreed very closely with the calculated values of the chromene compound (C)(84.19% of C, 5.30% of H, 1.89% of N and 8.63% of O). When the proton nuclear magnetic resonance spectrum of the crystal was measured, only a peak derived from the chromene compound (C) shown in Example 1 was confirmed. It could be confirmed from the above results that the crystal was the chromene compound (C) and that it did not form a molecular compound with ethyl acetate unlike Example 1. The melting point and dissolution speed of the product were measured in the same manner as in Example 1 except that the amount of the product to be added to the monomer solution to obtain its dissolution speed was changed to 0.5 part by weight. The results are shown in Table 2. The chart of the differential thermal analysis of the product is shown in FIG. 3 for comparison with the molecular compound of Example 1.

Comparative Example 2

1 g of the purified chromene compound (D) obtained in Production Example 2 was dissolved in 10 ml of acetonitrile by heating and stirred overnight at room temperature. The precipitated powder was filtered and dried at 80° C. under reduced pressure until a weight reduction was not seen to produce 0.89 g of an orange crystal.

The elemental analysis values of the crystal were 75.89% of C, 5.89% of H, 3.76% of F, 5.44% of N and 9.22% of O which agreed very closely with the calculated values of the chromene compound (D)(75.84% of C, 5.98% of H, 3.64% of F, 5.36% of N and 9.18% of O). When the proton nuclear magnetic resonance spectrum of the crystal was measured, only a peak derived from the chromene compound (D) shown in Example 2 was confirmed.

It could be confirmed from the above results that the crystal was the chromene compound (D) and that it did not form a molecular compound with acetonitrile unlike Example 2.

The melting point and dissolution speed of the product were measured in the same manner as in Example 1 except that the amount of the product to be added to the monomer solution to obtain its dissolution speed was changed to 0.5 part by weight. The results are shown in Table 2.

TABLE 2

| No. | Chromene compound | properties of chromene compound | |
|---|---|---|---|
| | | melting point (° C.) | amount/dissolution speed (parts by weight)/(hour) |
| C.Ex.1 | 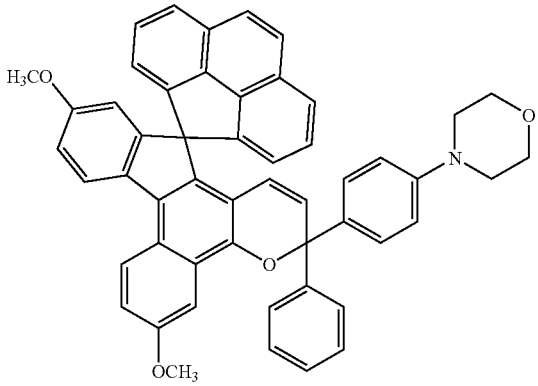 | 273 | 0.5/84 |
| C.Ex.2 | 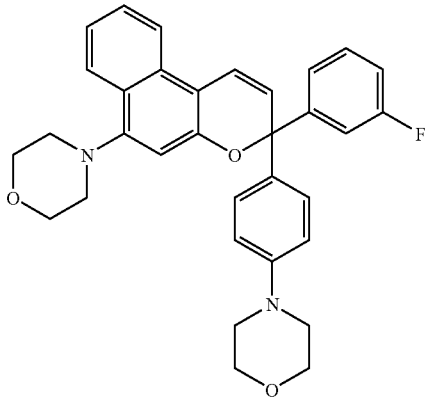 | 185 | 0.5/2 |

C.Ex.: Comparative Example

When Table 1 and Table 2 are compared with each other, Examples have a lower melting point than Comparative Examples and 10 times or more faster dissolution speed than Comparative Examples although the amount is 10 times larger.

Example 3

0.02 part by weight of 2,4,6-trimethylbenzoyldiphenyl phosphine oxide as a photopolymerization initiator and 0.5 part by weight of t-butylperoxy-2-ethyl hexanoate as a thermopolymerization initiator were added to 100 parts by weight of the monomer solution containing the molecular compound used for the measurement of dissolution speed in Example 1, fully mixed together and deaerated under reduced pressure. This mixed solution was poured into a mold formed using a glass plate and a gasket made from ethylene-vinyl acetate copolymer and exposed to an activation energy ray from a distance of 25 cm on both sides for 1 minute using a 1.5 kw metal halide lamp (with a heat ray cut filter) to carry out photopolymerization. Thereafter, the molded product was cured at 110° C. in a polymerization furnace for 1 hour and separated from a glass mold to obtain a 0.1 mm-thick photochromic polymer.

The obtained 0.1 mm-thick photochromic polymer was exposed to electron beams having an intensity on the surface of the polymer of 2.4 mW/cm$^2$ at 365 nm and 24 μW/cm$^2$ at 245 nm using the L-2480 SHL-100 xenon lamp (300 W) of Hamamatsu Photonics Co., Ltd. through an aeromass filter (of Corning Co., Ltd.) at 20° C.±1° C. for 120 seconds to develop a color and measure its photochromism. The photochromism was expressed by the following.

(1) maximum absorption wavelength (λmax): λmax after the color development of this polymer was obtained by the spectrophotometer (MCPD1000 instantaneous multi-channel photodetector) of Otsuka Denshi Kogyo Co., Ltd.

(2) color development intensity $\{\epsilon(120)-\epsilon(0)\}$: the difference between absorbance $\epsilon(120)$ after 120 seconds of exposure at the above maximum absorption wavelength and $\epsilon(0)$. It can be said that as this value becomes larger, photochromism is better. A photochromic polymer preferably has a color development intensity of 1.0 or more when it is used as an ordinary light control spectacle material.

(3) Fading speed [τ1/2 (min.)]: the time required for the absorbance of this polymer to be reduced to half of $\{\epsilon(120)-\epsilon(0)\}$ after 120 seconds of exposure. It can be said that as this time becomes shorter, photochromism is better.

The results are shown in Table 3.

Example 4

The procedure of Example 3 was repeated except that 100 parts by weight of the monomer solution (photochromic monomer) containing the molecular compound used for the measurement of dissolution speed in Example 2 was used as the photochromic monomer. The results are shown in Table 3.

TABLE 3

| No. | Molecular compound No. | amount of molecular compound (parts by weight) | λmax (nm) | color development intensity ε(120)–ε(0) | fading speed τ½ (min.) |
|---|---|---|---|---|---|
| Ex. 3 | Ex. 1 | 5 | 610 | 1.15 | 2.1 |
| Ex. 4 | Ex. 2 | 5 | 472 | 1.08 | 2.8 |

Ex.: Example

Comparative Example 3

The procedure of Example 3 was repeated except that the photochromic monomer prepared in Comparative Example 1 was used as the photochromic monomer. The results are shown in Table 4.

Comparative Example 4

The procedure of Example 3 was repeated except that the photochromic monomer prepared in Comparative Example 2 was used as the photochromic monomer. The results are shown in Table 4.

TABLE 4

| No. | Chromene compound No. | amount of chromene compound (parts by weight) | λmax (nm) | color development intensity ε(120)–ε(0) | fading speed τ½ (min.) |
|---|---|---|---|---|---|
| C. Ex. 3 | C. Ex. 1 | 0.5 | 610 | 0.42 | 1.8 |
| C. Ex. 4 | C. Ex. 2 | 0.5 | 472 | 0.33 | 2.5 |

C. Ex.: Comparative Example

As understood from Table 3 and Table 4, since the content of the chromene compound in the photochromic polymer was about 10 times higher in Examples than in Comparative Examples, the polymers of Examples showed excellent photochromism with higher color development intensity even when they were as thin as 0.1 mm.

Example 5

0.02 part by weight of 2,4,6-trimethylbenzoyldiphenylphosphine oxide as a photopolymerization initiator and 0.5 part by weight of t-butylperoxy-2-ethyl hexanoate as a thermopolymerization initiator were added to 100 parts by weight of the photochromic monomer prepared in Example 1 as a photochromic monomer, fully mixed together and deaerated under reduced pressure. This mixed solution was poured into a mold formed using a glass plate, an ADC resin board (thickness of 2.0 mm) and a gasket made from ethylene-vinyl acetate copolymer and exposed to an activation energy ray from a distance of 25 cm on both sides for 1 minute using a 1.5 kw metal halide lamp (with a heat ray cut filter) to carry out photopolymerization. Thereafter, the molded product was cured at 110° C. in a polymerization furnace for 1 hour and separated from a glass mold to obtain an ADC resin having a 0.1 mm-thick photochromic polymer on one side. When the photochromism of this optical material was evaluated in the same manner as in Example 3, it was almost equivalent to that of Example 3.

Example 6

The entire convex surface of a 2 mm-thick plastic lens (resin substrate: CR39) was subjected to an atmospheric-pressure plasma treatment for 90 seconds using an atmospheric-pressure plasma exposure unit (ST-7000 of Keyence Co., Ltd.). The distance between the exposure site and the lens was about 10 mm and a SUS mesh sheet was inserted between the exposure site and the lens. Nitrogen obtained from a commercially available nitrogen cylinder was used as the introduction gas for the plasma treatment. When the relative humidity of air supplied from the nitrogen cylinder was measured, it was 14% at 24° C. (temperature/humidity meter of Iuchi Seieido Co., Ltd.: TR-72S).

Subsequently, 5 parts by weight of the molecular compound (C), 0.4 part by weight of CGI184 as a photopolymerization initiator and 0.1 part by weight of CGI403 (as for abbreviations, refer to Example 7) were added to 100 parts by weight of polymerizable monomers consisting of 50 parts by weight of polyethylene glycol diacrylate having an average molecular weight of 532 and 50 parts by weight of glycidyl methacrylate, and stirred and mixed together at room temperature for 12 hours.

About 2 g of the mixed solution obtained by the above method was applied to the surface of a plastic lens (CR39) subjected to the above plasma treatment with the 1H-DX2 spin coater of MIKASA Co., Ltd. at a revolution speed of 60 rpm for 40 seconds, 500 rpm for 2 seconds and 1,000 rpm for 2 seconds. This lens having the coated surface was exposed to light using a metal halide lamp having an output of 120 mW/cm$^2$ in an nitrogen gas atmosphere for 2 minutes to cure the coating film. Thereafter, the lens was further heated at 110° C. for 2 hours. The composition of the used compound is shown in Table 5.

Using the obtained lens having a photochromic coating layer as a sample, the maximum absorption wavelength, color development intensity and fading speed of the photochromic coating layer, adhesion between the photochromic coating layer and the lens and the thickness of the coating layer were measured by the following methods.

The maximum absorption wavelength (1), color development intensity (2) and fading speed (3) were evaluated in the same manner as in Example 3.

(4) developed color: The developed color is evaluated outdoors by the eye.

(5) uniformity of photochromic coating layer: It is evaluated by the eye whether the precipitated crystal is existent in the photochromic coating layer after the end of polymerization. When no crystal precipitation is seen in the molecular compound or the photochromic compound and the photochromic coating layer is amorphous, it is judged as ○ and when crystal precipitation is apparent and the photochromic coating layer looks cloudy, it is evaluated as X.

(6) color development nonuniformity: Color is developed from the lens sample with sunlight outdoors and it is evaluated whether color development is uniform or not by the eye. When color development is uniform, it is judged as ○ and when color development is not uniform, it is judged as X.

(7) adhesion between lens and photochromic coating layer (adhesion 1): One hundred 1 mm×1 mm squares are formed by cutting the surface of the coating layer of the lens having a photochromic coating layer by a sharp cutting knife. Then, commercially available Cellotape is affixed to the surface and stripped off quickly to check the stripped state of the coating layer (coating film) by the eye. When all the squares still adhere to the surface, adhesion is judged as ○, when some of the squares are removed, adhesion is judged as Δ, and when all the squares are removed, adhesion is judged as X.

(8) thickness of photochromic layer: This is measured using the thin film measuring instrument of Filmetrics Co., Ltd.

Subsequently, the lens having a photochromic coating layer obtained by the above process is cleaned with acetone, dried with air completely to obtain a clear state, immersed in a 10% NaOH aqueous solution for 10 minutes, rinsed fully with water and dried with air again. This lens is immersed in the TS56H hard coat solution (condensation hard coat material of Tokuyama Corporation), pulled up at a rate of 30 mm/min, pre-dried at 60° C. for 15 minuets and cured by heating at 120° C. for 3 hours to obtain a sample having a hard coat layer. Using this sample, adhesion between the photochromic coating layer and the hard coat material is evaluated.

(9) adhesion between photochromic coating layer and hard coat material (adhesion 2): One hundred 1 mm² squares are formed on the surface (covered with a hard coat layer) on a photochromic layer side of the hard coated lens by a sharp cutting knife and commercially available Cellotape is affixed to the surface and stripped off quickly to check the stripped states of the hard coat layer and the photochromic coating layer by the eye. When all the squares still adhere to the surface, adhesion is judged as ○, when some of the squares are removed, adhesion is judged as Δ, and when all the squares are removed, adhesion is judged as X. The results are shown in Table 7.

Examples 7 to 15

The procedure of Example 6 was repeated to obtain a lens having a photochromic coating layer except that the types and amounts of the radically polymerizable monomer, amine compound, molecular compound, photochromic compound (chromene compound, spirooxazine compound), polymerization initiator and stabilizer used to prepare a coating and the type of the resin substrate were changed as shown in Table 5, and the lens was evaluated in the same manner as in Example 6. The results are shown in Table 7.

In Table 5, the used compounds are expressed by abbreviations. Each abbreviation represents the following compound. As for the other radically polymerizable monomers, the L-scale Rockwell hardness of a cured product obtained by cast homopolymerizing each compound (monomer) (polymerized by heating from 30° C. to 90° C. over 20 hours and further polymerized by heating at 120° C. for 2 hours) is given as "homo-HL" within parentheses. As for the method of measuring the hardness, the hardness is measured with an Akashi Rockwell hardness meter (type: AR-10) after a cured product is kept in a chamber maintained at 25° C. for 1 day. Glycidyl methacrylate is an epoxy-based monomer.

(1) Radically Polymerizable Monomers

TMPT: trimethylolpropane trimethacrylate (homo-HL=122)
DPEHA: dipentaerythritol hexaacrylate (homo-HL=100)
U6A: urethane oligomer hexaacrylate (homo-HL=100) (Shin-Nakamura Kagakusha: U-6HA)
EB6A: polyester oligomer hexaacrylate (homo-HL=100) (Daicel UCB: EB1830)
GMA: glycidyl methacrylate (homo-HL=80)
BPE: 2,2-bis(4-methacryloyloxyethoxyphenyl)propane (homo-HL=110)
DVB: divinylbenzene (homo-HL=110)
BSA: (homo-HL=105)

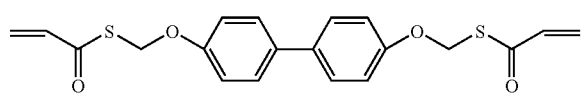

BBA: (homo-HL=80)

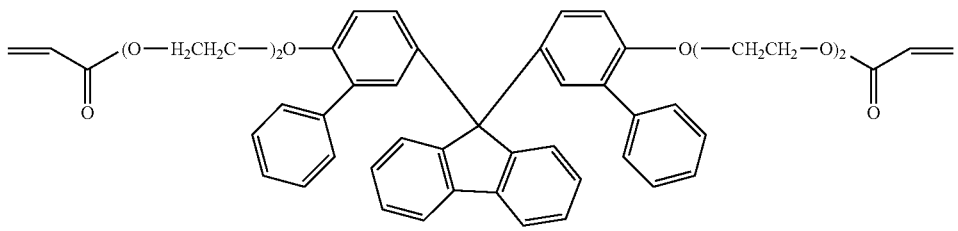

BZMA: benzyl methacrylate (homo-HL=80)
9GDA: polyethylene glycol diacrylate having an average molecular weight of 532 (homo-HL<20)

MePEGMA (475): methyl ether polyethylene glycol methacrylate having an average molecular weight of 1,000 (homo-HL<20)

BPE oligomer: 2,2-bis(4-acryloyloxypolyethylene glycol phenyl)propane having an average molecular weight of 776 (homo-HL<40)-silyl monomer
TMSiMA: γ-methacryloyloxypropyltrimethoxysilane
DMSiMA: γ-methacryloyloxypropylmethyldimethoxysilane-isocyanate monomer
MOI: 2-isocyanatoethoxy methacrylate (2) Amine Compounds
NMDEA: N-methyldiethanolamine
DMEMA: N,N-dimethylaminoethyl methacrylate (3) Molecular Compounds
molecular compound (C): molecular compound of chromene (C) and toluene obtained in Example 1
molecular compound (D): molecular compound of chromene (D) and toluene obtained in Example 2

(4) Photochromic Compounds
chromene (A)
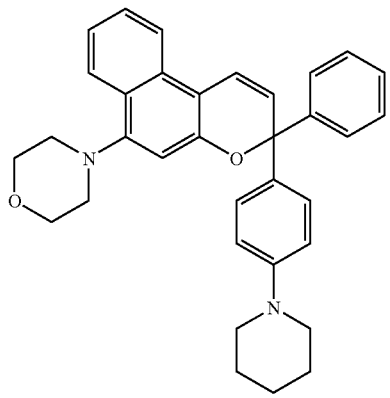
chromene (B)
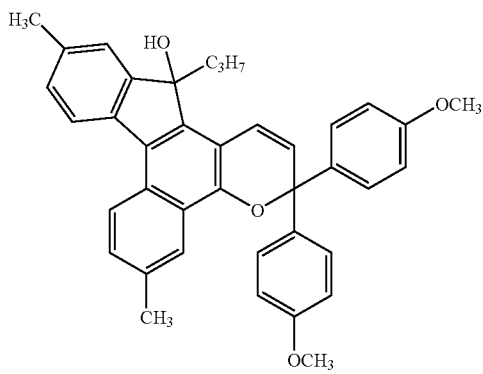
chromene (C): chromene compound obtained in Production Example 1
chromene (D): chromene compound obtained in Production Example 2
chromene (E)
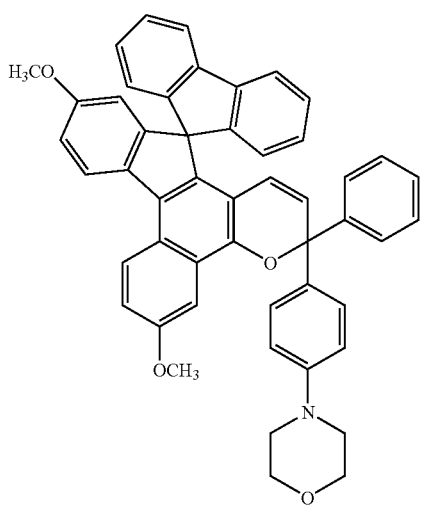
chromene (F)
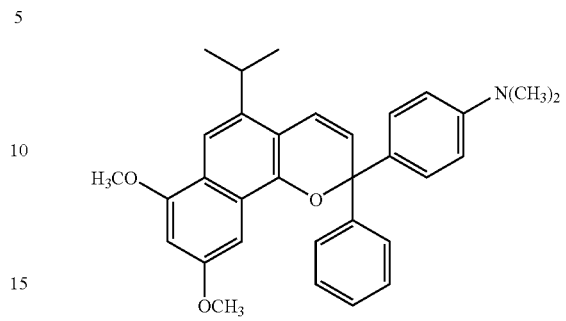
chromene (G)
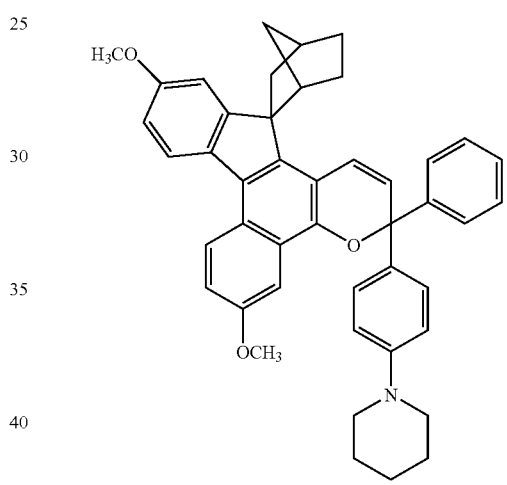
spirooxazine (A)
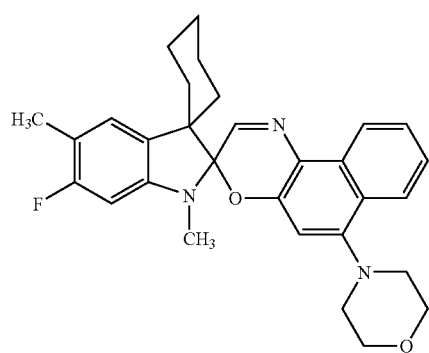

spirooxazine (B)

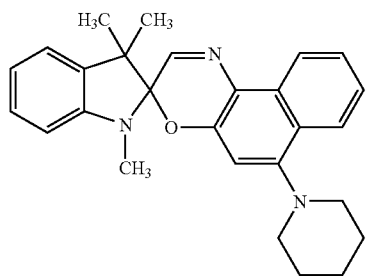

(5) Polymerization Initiators
CGI184: 1-hydroxycyclohexylphenyl ketone
CGI403: bis(2,6-dimethoxybenzoyl)-2,4,4-trimethyl-pentylphosphine oxide
Perbutyl O: t-butylperoxy-2-ethyl hexanoate
(6) Stabilizers
LS765: bis(1,2,2,6,6-pentamethyl-4-piperidyl)sebacate (7) Optical Materials
CR39: (allyl resin plastic lens; refractive index=1.50)
MR (thiourethane-based resin plastic lens; refractive index=1.60)
TE (thioepoxy-based resin plastic lens; refractive index=1.71)
SPL (methacrylic resin plastic lens; refractive index=1.54)

Comparative Examples 3 and 4

A lens having a photochromic coating layer was obtained in the same manner as in Example 6 except that a radically polymerizable monomer, amine compound, photochromic compound, polymerization initiator, stabilizer and resin substrate were changed as shown in Table 6 and that a molecular compound was not used.

Since the molecular compound was not used, they were not dissolved in high concentrations but cured as a slurry solution.

The obtained lens was evaluated by the above evaluation methods and the obtained results are shown in Table 8.

TABLE 5

| Ex. No. | Radically polymerizable monomer (parts by weight) | silyl monomer/ isocyanate monomer (parts by weight) | amine compound (parts by weight) | polymerization initiator (parts by weight) |
|---|---|---|---|---|
| 6 | 9GDA/GMA 50/50 | — | — | CGI184/CGI403 0.4/0.1 |
| 7 | 9GDA/GMA 50/50 | — | — | CGI184/CGI403 0.4/0.1 |
| 8 | 9GDA/GMA 50/50 | — | — | CGI184/CGI403 0.4/0.1 |
| 9 | 9GDA/DVB/GMA 40/40/20 | — | — | CGI184/CGI403 0.4/0.1 |
| 10 | TMPT/BPE/U6A/9GDA/GMA 20/39/10/20/10 | TMSiMA 1 | NMDEA 0.1 | CGI184/Perbutyl O 0.5/0.1 |
| 11 | DPEHA/BPEoligomer/EB6A/9GA/GMA 20/37/10/20/10 | DMSiMA 3 | NMDEA 3 | CGI184/CGI403 1/0.1 |
| 12 | BBA/BPE/TMPT/MePEGMA/GMA 35/35/10/8/10 | MOI 2 | DMDEA 2 | CGI403/Perbutyl O 0.05/1 |
| 13 | BSA/BzMA/TMPT/9GDA/GMA 35/35/10/7/10 | TMSiMA 3 | NMDEA 5 | CGI403/Perbutyl O 0.01/1 |
| 14 | BPEoligomer/TMPT/EB6A/9GDA/GMA 35/15/15/15/10 | TMSiMA 7 | NMDEA 3 | CGI184/CGI403 0.4/0.1 |
| 15 | BPEoligomer/TMPT/EB6A/9GDA/GMA 35/15/15/15/10 | TMSiMA 7 | NMDEA 3 | CGI184/CGI403 0.4/0.1 |

| Ex. No. | Stabilizer (parts by weight) | optical material | molecular compound (parts by weight) | chromene compound (parts by weight) | spirooxazine compound (parts by weight) |
|---|---|---|---|---|---|
| 6 | — | CR39 | (C) 5 | — | — |
| 7 | — | CR39 | (D) 5 | — | — |
| 8 | — | MR | (C) 10 | — | — |
| 9 | — | MR | (C) 15 | — | — |
| 10 | LS765 5 | TE | (C) 5 | — | — |
| 11 | LS765 5 | SPL | (D) 3 | (G) 2 | — |
| 12 | LS765 5 | SPL | (C)/(D) 5/3 | (A) 0.5 | — |
| 13 | LS765 5 | CR39 | (C)/(D) 5/2 | (B)/(E)/(F) 0.5/0.5/0.3 | — |
| 14 | LS765 5 | MR | (C)/(D) 3/0.9 | (B) 0.6 | (A)/(B) 0.3/0.3 |
| 15 | LS765 5 | MR | (C)/(D) 1.6/2.4 | (B) 0.2 | (A)/(B) 0.2/0.2 |

Ex.: Example

TABLE 6

| C. Ex. No. | Radically polymerizable monomer (parts by weight) | silyl monomer/ isocyanate monomer (parts by weight) | amine compound (parts by weight) | polymerization initiator (parts by weight) |
|---|---|---|---|---|
| 3 | 9GDA/GMA 50/50 | — | — | CGI184/CGI403 0.4/0.1 |
| 4 | 9GDA/GMA 50/50 | — | — | CGI184/CGI403 0.4/0.1 |

| C. Ex. No. | Stabilizer (parts by weight) | optical material | molecular compound (parts by weight) | chromene compound (parts by weight) | spirooxazine compound (parts by weight) |
|---|---|---|---|---|---|
| 3 | — | CR39 | — | (C) 5 | — |
| 4 | — | CR39 | — | (D) 5 | — |

C. Ex.: Comparative Example

TABLE 7

| Ex. No. | λmax (nm) | Color development intensity | fading speed (min) | developed color | uniformity | color development nonuniformity | adhesion 1 (substrate) | film thickness (μm) | adhesion 2 (hard coat) |
|---|---|---|---|---|---|---|---|---|---|
| 6 | 610 | 0.66 | 1.3 | Blue | ○ | ○ | ○ | 15 | ○ |
| 7 | 470 | 0.60 | 1.9 | Orange | ○ | ○ | ○ | 15 | ○ |
| 8 | 610 | 0.81 | 1.4 | Blue | ○ | ○ | ○ | 18 | ○ |
| 9 | 610 | 0.93 | 1.8 | Blue | ○ | ○ | Δ | 20 | Δ |
| 10 | 610 | 0.82 | 1.4 | Blue | ○ | ○ | ○ | 32 | ○ |
| 11 | 470 | 0.77 | 1.9 | Amber | ○ | ○ | ○ | 40 | ○ |
|    | 598 | 0.67 | 1.3 |       |   |   |   |    |   |
| 12 | 476 | 0.65 | 1.8 | Gray | ○ | ○ | ○ | 28 | ○ |
|    | 610 | 0.72 | 1.4 |      |   |   |   |    |   |
| 13 | 470 | 0.62 | 1.9 | Gray | ○ | ○ | ○ | 25 | ○ |
|    | 610 | 0.70 | 1.4 |      |   |   |   |    |   |
| 14 | 472 | 0.80 | 1.9 | Gray | ○ | ○ | ○ | 40 | ○ |
|    | 610 | 0.83 | 1.3 |      |   |   |   |    |   |
| 15 | 470 | 0.90 | 1.9 | Brown | ○ | ○ | ○ | 41 | ○ |
|    | 610 | 0.78 | 1.3 |       |   |   |   |    |   |

Ex.: Example

TABLE 8

| C. Ex. No. | λmax (nm) | Color development intensity | fading speed (min) | developed color | uniformity | color development nonuniformity | adhesion 1 (substrate) | film thickness (μm) | adhesion 2 (hard coat) |
|---|---|---|---|---|---|---|---|---|---|
| 3 | 610 | 0.2 | 3.0 | Blue | X | X | X | 17 | X |
| 4 | 470 | 0.11 | 3.5 | Orange | X | X | X | 14 | X |

C. Ex.: Comparative Example

The curable composition and coating composition comprising a molecular compound of the present invention have extremely high solubility in monomers and the like and are easily dispersed in a polymer matrix uniformly in a high concentration, making use of this property. Therefore, especially for applications that require small thickness, for example, when a thin film of a photochromic polymer is formed and used to control light, the content of the photochromic compound can be increased, thereby making it possible to obtain a thin film having excellent photochromism.

The invention claimed is:

1. A photochromic composition obtained by mixing together (1) 100 parts by weight of a radically polymerizable monomer or a polymer compound and (2) 0.01 to 20 parts by weight of a molecular compound of a chromene compound and an aromatic compound.

2. The composition of claim 1 which further comprises 10 parts or less by weight of a photochromic compound.

3. The composition of claim 1, wherein the molecular compound is a molecular compound of a chromene compound represented by the following formula (1):

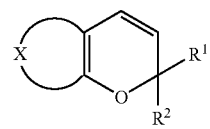

(1)

wherein $R^1$ and $R^2$ are each a substituted or nonsubstituted aryl group, or a substituted or nonsubstituted aromatic heterocyclic group, and the divalent group represented by the following formula (2) is a divalent condensed polycyclic organic group which has a benzene ring condensed to the 2H-pyran ring in the above formula (1) and may have a substituent,

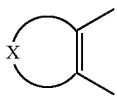 (2)

and an aromatic compound having a molecular weight of 70 to 150.

4. The composition of claim 1 which is obtained by mixing together 100 parts by weight of a radically polymerizable monomer and 0.01 to 20 parts by weight of the above molecular compound and further comprises 0.001 to 10 parts by weight of a photopolymerization initiator.

5. A coating composition obtained by mixing together (1) 100 parts by weight of a radically polymerizable monomer, (2) 1 to 30 parts by weight of a molecular compound of a chromene compound and an aromatic compound, or a combination of this molecular compound and a photochromic compound, and (3) 0.01 to 10 parts by weight of a photopolymerization initiator, the number of parts by weight of the component being smaller than the number of parts by weight of the component (2).

6. The coating composition of claim 5, wherein the amount of the photochromic compound is 10 parts or less by weight based on 1 to 30 parts by weight of the total of the molecular compound and the photochromic compound.

7. The coating composition of claim 5, wherein the molecular compound is a molecular compound of a chromene compound represented by the following formula (1):

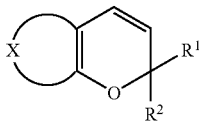 (1)

wherein $R^1$ and $R^2$ are each a substituted or nonsubstituted aryl group, or a substituted or nonsubstituted aromatic heterocyclic group, and the divalent group represented by the following formula (2) is a divalent condensed polycyclic organic group which has a benzene ring condensed to the 2H-pyran ring in the above formula (1) and may have a substituent,

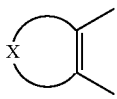 (2)

and an aromatic compound having a molecular weight of 70 to 150.

8. A photochromic optical material which is a cured product of the composition of any one of claims 1 to 4.

9. A process for producing a photochromic optical material, comprising curing the composition of any one of claims 1 to 4.

10. A photochromic optical material comprising a substrate and a cured coating film of the coating composition of any one of claims 5 to 7 on at least one side of the substrate.

11. The photochromic optical material of claim 10 which is a photochromic lens comprising a lens as the substrate.

12. A process for producing a photochromic optical material, which comprises applying the coating composition of any one of claims 5 to 7 to at least one side of a substrate and curing the coating film by light or both light and heat.

13. The process of claim 12, wherein curing is carried out in the absence of molecular oxygen.

14. A molecular compound of a chromene compound represented by the following formula (1):

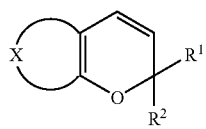 (1)

wherein $R^1$ and $R^2$ are each a substituted or nonsubstituted aryl group, or a substituted or nonsubstituted aromatic heterocyclic group, and the divalent group represented by the following formula (2) is a divalent condensed polycyclic organic group which has a benzene ring condensed to the 2H-pyran ring in the above formula (1) and may have a substituent,

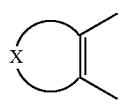 (2)

and an aromatic compound having a molecular weight of 70 to 150.

15. A process for producing a molecular compound, comprising contacting an aromatic compound having a molecular weight of 70 to 150 to a chromene compound represented by the above formula (1) in a solution to precipitate a molecular compound of the chromene compound and the aromatic compound as a crystal.

* * * * *